United States Patent
Pinton et al.

(10) Patent No.: US 12,150,813 B2
(45) Date of Patent: Nov. 26, 2024

(54) METHODS, SYSTEMS, AND COMPUTER READABLE MEDIA FOR GENERATING SUPER-RESOLUTION IMAGES OF MICROVASCULATURE USING ULTRASOUND

(71) Applicant: The University of North Carolina at Chapel Hill, Chapel Hill, NC (US)

(72) Inventors: Gianmarco Francesco Pinton, Chapel Hill, NC (US); Thomas Montgomery Kierski, Durham, NC (US); David Antonio Espindola Rojas, Chapel Hill, NC (US); Paul Alexander Dayton, Carrboro, NC (US); Isabel Grace Newsome, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 33 days.

(21) Appl. No.: 17/606,986

(22) PCT Filed: May 11, 2020

(86) PCT No.: PCT/US2020/032406
§ 371 (c)(1),
(2) Date: Oct. 27, 2021

(87) PCT Pub. No.: WO2020/231954
PCT Pub. Date: Nov. 19, 2020

(65) Prior Publication Data
US 2022/0211350 A1    Jul. 7, 2022

Related U.S. Application Data

(60) Provisional application No. 62/846,133, filed on May 10, 2019.

(51) Int. Cl.
*A61B 8/08* (2006.01)

(52) U.S. Cl.
CPC .......... *A61B 8/5207* (2013.01); *A61B 8/0891* (2013.01); *A61B 8/481* (2013.01)

(58) Field of Classification Search
CPC ........................... G01S 7/52039; A61B 8/481
See application file for complete search history.

(56) References Cited

U.S. PATENT DOCUMENTS

| 4,816,567 A | 3/1989 | Cabilly et al. |
| 5,088,499 A | 2/1992 | Unger |

(Continued)

FOREIGN PATENT DOCUMENTS

| CA | 2 773 181 | 2/2018 |
| JP | 2011/015952 A | 1/2011 |

(Continued)

OTHER PUBLICATIONS

C. Errico et al, "Ultrafast ultrasound localization microscopy for deep super-resolution vascular imaging", Nature, vol. 527, pp. 499-502, Nov. 2015 (Year: 2015).*

(Continued)

*Primary Examiner* — Joel Lamprecht
*Assistant Examiner* — Nyrobi Celestine
(74) *Attorney, Agent, or Firm* — Jenkins, Taylor & Hunt, P.A.

(57) ABSTRACT

A method for producing an image of a vessel with ultrasound includes administering a contrast agent particle into the vessel and delivering an ultrasound pulse having a first frequency range to the vessel. The method further includes detecting ultrasound energy scattered from the contrast agent particle at a second frequency range, converting the scattered ultrasound energy into an electronic radio frequency signal, and using an algorithm to determine a spatial (Continued)

location of the contrast agent particle based on extraction of a specific feature of the radio frequency signal. The method further includes generating an image by displaying a marker of the spatial location of the contrast agent particle with a resolution that is finer than a pulse length of the ultrasound pulse and repeating the steps for different contrast agent particles until sufficient markers have been accumulated to reconstruct a pattern of the vessel.

38 Claims, 16 Drawing Sheets

(56) References Cited

U.S. PATENT DOCUMENTS

| | | |
|---|---|---|
| 5,147,631 A | 9/1992 | Glajch et al. |
| 5,577,505 A | 11/1996 | Brock-Fisher et al. |
| 5,740,596 A | 4/1998 | Corl et al. |
| 5,879,303 A | 3/1999 | Averkiou et al. |
| 5,906,580 A | 5/1999 | Kline-Schoder et al. |
| 5,951,478 A | 9/1999 | Hwang et al. |
| 6,172,197 B1 | 1/2001 | McCafferty et al. |
| 6,221,018 B1 | 4/2001 | Ramamurthy et al. |
| 6,231,834 B1 | 5/2001 | Unger et al. |
| 6,245,318 B1 | 6/2001 | Klibanov et al. |
| 6,248,516 B1 | 6/2001 | Winter et al. |
| 6,254,852 B1 | 7/2001 | Glajch et al. |
| 6,291,158 B1 | 9/2001 | Winter et al. |
| 6,312,383 B1 | 11/2001 | Lizzi et al. |
| 6,409,667 B1 | 6/2002 | Hossack |
| 6,740,039 B1 | 5/2004 | Rafter et al. |
| 7,051,654 B2 | 5/2006 | Boland et al. |
| 7,358,226 B2 | 4/2008 | Dayton et al. |
| 8,090,164 B2 | 1/2012 | Bullitt et al. |
| 8,233,681 B2 | 7/2012 | Aylward et al. |
| 9,340,581 B2 | 5/2016 | Hallahan et al. |
| 9,375,397 B2 | 6/2016 | Bettinger et al. |
| 9,532,769 B2 * | 1/2017 | Dayton ............... G01S 7/52047 |
| 2003/0092991 A1 | 5/2003 | Sehgal |
| 2004/0087858 A1 | 5/2004 | Hao et al. |
| 2005/0038423 A1 | 2/2005 | Makin et al. |
| 2005/0084538 A1 | 4/2005 | Dayton et al. |
| 2005/0277835 A1 * | 12/2005 | Angelsen ............ G01S 7/52095 |
| | | 600/437 |
| 2006/0078501 A1 | 4/2006 | Goertz et al. |
| 2006/0241462 A1 * | 10/2006 | Chou ..................... A61B 8/481 |
| | | 600/455 |
| 2007/0035204 A1 | 2/2007 | Angelsen et al. |
| 2008/0045865 A1 | 2/2008 | Kislev |
| 2008/0182237 A1 | 7/2008 | Bentwich et al. |
| 2008/0319375 A1 | 12/2008 | Hardy |
| 2009/0076394 A1 | 3/2009 | Wong et al. |
| 2009/0182237 A1 | 7/2009 | Bjorn et al. |
| 2010/0196284 A1 * | 8/2010 | Lindner ................... A61K 9/10 |
| | | 424/9.1 |
| 2011/0250688 A1 | 10/2011 | Hasan |
| 2012/0035742 A1 | 2/2012 | Vunjak-Novakovic et al. |
| 2012/0220869 A1 * | 8/2012 | Dayton ............... G01S 7/52039 |
| | | 600/431 |
| 2013/0177972 A1 | 7/2013 | Green et al. |
| 2014/0142468 A1 * | 5/2014 | Hossack ................... A61N 7/00 |
| | | 601/2 |
| 2014/0236005 A1 | 8/2014 | Chen et al. |
| 2015/0141833 A1 * | 5/2015 | Dayton ................. A61B 8/4477 |
| | | 600/463 |
| 2015/0151142 A1 | 6/2015 | Tyler et al. |
| 2016/0106395 A1 * | 4/2016 | Hynynen .................. A61B 8/54 |
| | | 600/431 |
| 2017/0050076 A1 | 2/2017 | Beals |
| 2017/0198252 A1 | 7/2017 | Mironov et al. |
| 2018/0368810 A1 * | 12/2018 | Sboros ............... G01S 7/52036 |
| 2019/0069879 A1 * | 3/2019 | Foster ................. G01S 7/52039 |
| 2019/0242896 A1 | 8/2019 | Gessner et al. |
| 2020/0178939 A1 * | 6/2020 | Song ..................... A61B 8/0891 |
| 2021/0374910 A1 * | 12/2021 | Song ....................... A61B 8/481 |

FOREIGN PATENT DOCUMENTS

| | | | |
|---|---|---|---|
| WO | WO 92/22653 | 12/1992 | |
| WO | WO 2005/023086 A2 | 3/2005 | |
| WO | WO 2011/029094 A2 | 3/2011 | |
| WO | WO 2017/214637 A1 | 12/2017 | |
| WO | WO-2018042191 A1 * | 3/2018 | ............... A61B 8/06 |
| WO | WO-2018045373 A1 * | 3/2018 | ............. B33Y 40/00 |

OTHER PUBLICATIONS

Y. Li et al, "An Integrated System for Superharmonic Contrast-Enhanced Ultrasound Imaging: Design and Intravascular Phantom Imaging Study", IEEE Transactions on Biomedical Engineering, vol. 63, No. 9, pp. 1933-1943, Sep. 2016 (Year: 2016).*

J. Foiret et al, "Ultrasound localization microscopy to image and assess microvasculature in a rat kidney", Scientific Reports, vol. 7, No. 13662, pp. 1-12, Oct. 2017 (Year: 2017).*

F. Lin et al, "3-D Ultrasound Localization Microscopy for Identifying Microvascular Morphology Features of Tumor Angiogenesis at a Resolution Beyond the Diffraction Limit of Conventional Ultrasound", Theranostics, vol. 7, No. 1, pp. 196-204, Jan. 2017 (Year: 2017).*

J. Yu et al, "Super-resolution ultrasound imaging method for microvasculature in vivo with a high temporal accuracy", Scientific Reports, vol. 8, pp. 1-11, 2018 (Year: 2018).*

S. Wang et al, "Targeting of microbubbles: contrast agents for ultrasound molecular imaging", Journal of Drug Targeting, vol. 26, No. 5-6, pp. 420-434, Jan. 2018 (Year: 2018).*

A. Bar-Zion et al, "SUSHI: Sparsity-Based Ultrasound Super-Resolution Hemodynamic Imaging", IEEE Transactions on Ultrasonics, Ferroelectrics, and Frequency Control, vol. 65, No. 12, pp. 2365-2380, Dec. 2018 (Year: 2018).*

W. Guo et al, "A High-Efficiency Super-Resolution Reconstruction Method for Ultrasound Microvascular Imaging", Applied Sciences, vol. 8, No. 1143, pp. 1-12, Jul. 2018 (Year: 2018).*

Hingot et al., "Microvascular flow dictates the compromise between spatial resolution and acquisition time in Ultrasound Localization Microscopy," Scientific Reports, vol. 9, No. 2456, pp. 1-10 (2019).

Baranger et al., "Adaptive Spatiotemporal SVD Clutter Filtering for Ultrafast Doppler Imaging Using Similarity of Spatial Singular Vectors," IEEE Transactions on Medical Imaging, vol. 37, No. 7, pp. 1574-1586 (Jul. 2018).

Couture et al., "Ultrasound Localization Microscopy and Super-Resolution: a State of the Art," IEEE Transaction on Ultrasonics, Ferroelectrics, and Frequency Control, vol. 65, No. 8, pp. 1304-1320 (Aug. 2018).

Harput et al., "Two-Stage Motion Correction for Super-Resolution Ultrasound Imaging in Human Lower Limb," IEEE Transactions on Ultrasonics, Ferroelectrics, and Frequency Control, vol. 65, No. 5, pp. 803-814 (May 2018).

Lindsey et al., "Dual-Frequency Piezoelectric Endoscopic Transducer for Imaging Vascular Invasion in Pancreatic Cancer," IEEE Trans Ultrason Ferroelectr Freq Control, vol. 64, No. 7, pp. 1-26 (2018).

Opacic et al., "Motion model ultrasound localization microscopy for preclinical and clinical multiparametric tumor characterization," Nature Communications, pp. 1-13 (2018).

Christensen-Jeffries et al., "Microbubble Axial Localization Errors in Ultrasound Super-Resolution Imaging," IEEE Transactions on Ultrasonics Ferroelectrics and Frequency Control, vol. 64, No. 11, pp. 1-14 (2017).

Desailly et al., "Contrast enhanced ultrasound by real-time spatiotemporal filtering of ultrafast images," Phys. Med. Biol., vol. 62, pp. 1-13 (2017).

Foiret et al., "Ultrasound localization microscopy to image and assess microvasculature in a rat kidney," Scientific Reports, vol. 7, pp. 1-12 (2017).

(56) References Cited

OTHER PUBLICATIONS

Lin et al., "3-D Ultrasound Localization Microscopy for Identifying Microvascular Morphology Features of Tumor Angiogenesis at a Resolution Beyond the Diffraction Limit of Conventional Ultrasound," Theranostics, vol. 7, Issue 1, pp. 1-10 (2017).

Shelton et al., "A first in human study of acoustic angiography in the breast and peripheral vasculature," Ultrasound Med Biol., vol. 42, No. 12, pp. 1-17 (Dec. 2017).

Tsuruta et al., "Optimizing ultrasound molecular imaging of secreted frizzled related protein 2 expression in angiosarcoma," PLoSONE, vol. 12, No. 3, pp. 1-21 (Mar. 2017).

Rao et al., "The 'fingerprint' of cancer extends beyond solid tumor boundaries: assessment with a novel ultrasound imaging approach," IEEE Trans Biomed Eng., vol. 63, No. 5, pp. 1-12 (May 2016).

Tremblay-Darveau et al., "Visualizing the Tumor Microvasculature with a Nonlinear Plane-Wave Doppler Imaging Scheme Based on Amplitude Modulation," IEEE Transactions on Medical Imaging, vol. 35, No. 2 pp. 699-709 (Feb. 2016).

Christensen-Jeffries et al., "In Vivo Acoustic Super-Resolution and Super-Resolved Velocity Mapping Using Microbubbles," IEEE Transactions on Medical Imaging, vol. 34, No. 2, pp. 1-10 (2015).

Demene et al., "Spatiotemporal Clutter Filtering of Ultrafast Ultrasound Data Highly Increases Doppler and fUltrasound Sensitivity," IEEE Transactions on Medical Imaging, vol. 34, No. 11, pp. 2271-2285 (Nov. 2015).

Desailly et al., "Resolution limits of ultrafast ultrasound localization microscopy," Phys. Med. Biol., vol. 60, pp. 1-20 (2015).

Errico et al., "Ultrafast ultrasound localization microscopy for deep super-resolution vascular imaging," Nature, vol. 527, pp. 1-10 (Nov. 26, 2015).

Shelton et al., "Quantification of microvascular tortuosity during tumor evolution utilizing acoustic angiography," Ultrasound Med Biol., vol. 41, No. 7, pp. 1-19 (Jul. 2015).

Lindsey et al., "Optimization of Contrast-to-tissue Ratio and Role of Bubble Destruction in Dual-Frequency Contrast-Specific 'Acoustic Angiography' Imaging," 2014 IEEE International Ultrasonics Symposium Proceedings, pp. 1774-1777 (2014).

Gessner et al., "Acoustic Angiography: a New Imaging Modality for Assessing Microvasculature Architecture," International Journal of Biomedical Imaging, pp. 1-10 (2013).

Caro et al., "The Mechanics of the Circulation," Cambridge University Press, Second Edition, pp. 1-26 (2012).

Gessner et al., "Mapping Microvasculature with Acoustic Angiography Yields Quantifiable Differences between Healthy and Tumor-bearing Tissue Volumes in a Rodent Model," Radiology, vol. 264, No. 3, pp. 733-740 (Sep. 2012).

Hanahan et al., "Hallmarks of Cancer: the Next Generation," Cell, vol. 144, pp. 1-29 (Mar. 4, 2011).

Luo et al., "A Fast Normalized Cross-Correlation Calculation Method for Motion Estimation," IEEE Trans Ultrason Ferroelectr Freq Control, vol. 57, No. 6, pp. 1-24 (Jun. 2010).

Van Neer et al., "Super-Harmonic Imaging: Development of an Interleaved Phased-Array Transducer," IEEE Transactions on Ultrasonics, Ferroelectrics, and Frequency Control, vol. 57, No. 2, pp. 455-468 (Feb. 2010).

Jong et al., "Ultrasonic characterization of ultrasound contrast agents," Med Biol Eng Comput, vol. 47, pp. 861-873 (2009).

Boukaz et al., "Super harmonic imaging: a new imaging technique for improved contrast detection," Ultrasound in Medicine & Biology, vol. 28, No. 1, pp. 1-11 (2002).

Phillips, "Contrast Pulse Sequences (CPS): Imaging Nonlinear Microbubbles," IEEE Ultrasonics Symposium, pp. 1739-1745 (2001).

Carmeliet et al., "Angiogenesis in cancer and other diseases," Nature, vol. 407, pp. 249-257 (Sep. 14, 2000).

Walker et al., "A Fundamental Limit on Delay Estimation Using Partially Correlated Speckle Signals," IEEE Transactions on Ultrasonics, Ferroelectrics, and Frequency Control, vol. 42, No. 2, pp. 301-308 (Mar. 1995).

Jong et al., "Higher harmonics of vibrating gas-filled microspheres. Part one: simulations," Ultrasonics, vol. 32, No. 6, pp. 447-453 (1994).

Fagrell et al., "A microscope-television system for studying flow velocity in human skim capillaries," Amer. J. Physiol. Heart Circulatory Physiol, pp. 1-4 (1977).

International Search Report for International Application No. PCT/US2020/032406 (Aug. 27, 2020).

Advisory Action for U.S. Appl. No. 16/327,726 (Jan. 22, 2024).

Applicant-Initiated Interview Summary for U.S. Appl. No. 16/327,726 (Dec. 21, 2023).

Johanna Jokinen et al., "Integrin-mediated Cell Adhesion to Type I Collagen Fibrils," Journal of Biological Chemistry, vol. 279, Issue 30; pp. 31956-31963; ISSN 0021-9258 (Jul. 23, 2004).

Final Office Action for U.S. Appl. No. 16/327,726 (Sep. 14, 2023).

Mercado et al., "Estimating Cell Concentration in Three-Dimensional Engineered Tissues Using High Frequency Quantitative Ultrasound," Ann Biomed Eng., vol. 42(6), p. 1292-1304 (2014).

Rychak et al., "Enhanced Targeting of Ultrasound Contrast Agents Using Acoustic Radiation Force," Ultrasound in Medicine and Biology, vol. 33, Issue 7, p. 1132-1139 (2007).

Takalkar et al., "Binding and Detachment Dynamics of Microbubbles Targeted to P-Selectin Under Controlled Shear Flow," Journal of Controlled Release, 96, p. 473-482 (2004).

Rychak et al., "Acoustic Radiation Force Enhances Targeted Delivery of Ultrasound Contrast Microbubbles: in Vitro Verification," IEEE Transactions on Ultrasonics, Ferroelectrics, and Frequency Control, vol. 52, No. 3, p. 421-433 (Mar. 2005).

Non-Final Office Action for U.S. Appl. No. 16/327,726 (Dec. 22, 2022).

Notification of Transmittal of the International Search Report and the Written Opinion of the International Searching Authority, or the Declaration for International Application No. PCT/US17/50076 (Jan. 12, 2018).

Nagao et al., "Ultrasound-Guided Photoacoustic Imaging-Directed Re-Endothelialization of Acellular Vasculature Leads to Improved Vascular Performance," Acta Biomater, vol. 32, pp. 35-45 (2016).

Shelton et al., "Molecular Acoustic Angiography: a New Technique for High Resolution Superharmonic Ultrasound Molecular Imaging," Ultrasound in Medicine & Biology, vol. 42, No. 3, pp. 1-26 (2016).

Collins et al., "United States Renal Data System Public Health Surveillance of Chronic Kidney Disease and End-Stage Renal Disease," Kidney International Supplements, vol. 5, pp. 2-7 (2015).

Keravnou et al., "Image-Guided Sonoporation in an Ex Vivo Machine Perfused Porcine Liver," J Ther Ultrasound, vol. 3, pp. 1-2 (2015).

Azene et al., "Tracking of Stem Cells in Vivo for Cardiovascular Applications," J Cardiovasc Magn Reson, vol. 16, No. 1, pp. 1-22 (2014).

Go et al., "Heart Disease and Stroke Statistics—2014 Update," Circulation, vol. 129, No. 3, pp. 1-536 (2014).

Dutta et al., "Non-Invasive Assessment of Elastic Modulus of Arterial Constructs During Cell Culture Using Ultrasound Elasticity Imaging," Ultrasound Med Biol, vol. 39, No. 11, pp. 1-23 (2013).

Gessner et al., "Functional Ultrasound Imaging for Assessment of Extracellular Matrix Scaffolds Used for Liver Organoid Formation," Biomaterials, vol. 34, pp. 1-24 (2013).

Streeter et al., "A Comparative Evaluation of Ultrasound Molecular Imaging, Perfusion Imaging, and Volume Measurements in Evaluating Response to Therapy in Patient-Derived Xenografts," Technol Cancer Res Treat., vol. 12, No. 4, pp. 1-20 (2013).

Yu et al., "Non-Invasive Characterization of Polyurethane-Based Tissue Constructs in a Rat Abdominal Repair Model Using High Frequency Ultrasound Elasticity Imaging," Biomaterials, vol. 34, No. 11, pp. 1-18 (2013).

Gessner et al., "An in Vivo Validation of the Application of Acoustic Radiation Force to Enhance the Diagnostic Utility of Molecular Imaging Using 3D Ultrasound," Ultrasound Med Biol., vol. 38, No. 4, pp. 1-18 (2012).

(56) References Cited

OTHER PUBLICATIONS

Gessner et al., "Mapping Microvasculature with Acoustic Angiography Yields Quantifiable Differences Between Healthy and Tumor-Bearing Tissue Volumes in a Rodent Model," Radiology, vol. 264, No. 3, pp. 733-740 (2012).
Pauwels et al., "Global Strategy for the Diagnosis, Management, and Prevention of Chronic Obstructive Pulmonary Disease," American Journal of Respiratory and Critical Care Medicine, vol. 163, pp. 1256-1276 (2001).
Popp et al., "An Instrumented Bioreactor for Mechanical Stimulation and Real-Time, Nondestructive Evaluation of Engineered Cartilage Tissue," Journal of Medical Devices, vol. 6, pp. 1-7 (Jun. 2012).
Puppi et al., "Improving the Techniques for Human Hepatocyte Transplantation," Report from a Consensus Meeting in London/Cell Transplantation, vol. 21, Issue 1, pp. 1-24 (2012).
Smith et al., "Kidney, Pancreas and Liver Allocation and Distribution in the United States," Am J of Transplant, vol. 12, pp. 1-36 (2012).
Badylak et al., "Whole-Organ Tissue Engineering: Decellularization and Recellularization of Three-Dimensional Matrix Scaffolds," Annu. Rev. Biomed. Eng., vol. 13, pp. 27-53 (2011).
Baptista et al., "The Use of Whole Organ Decellularization for the Generation of a Vascularized Liver Organoid," Hepatology, vol. 53, No. 2, pp. 604-617 (2011).
Gessner et al., "3D Microvessel-Mimicking Ultrasound Phantoms Produced with a Scanning Motion System," Ultrasound Med Biol., vol. 37, No. 5, pp. 1-12 (2011).
Kogan et al., "Validation of Dynamic Contrast-Enhanced Ultrasound in Rodent Kidneys as an Absolute Quantitative Method for Measuring Blood Perfusion," Ultra Med Biol., vol. 37, pp. 900-908 (2011).
Kooiman et al., "Sonoporation of endothelial cells by vibrating targeted microbubbles," J. Control Release, vol. 154, pp. 35-41 (2011).
Lalande et al., "Magnetic Resonance Imaging Tracking of Human Adipose Derived Stromal Cells Within Three-Dimensional Scaffolds for Bone Tissue Engineering," Eur Cell Mater, vol. 21, pp. 341-354 (2011).
Streeter et al., "Assessment of Molecular Imaging of Angiogenesis with Three-Dimensional Ultrasonography," Mol Imaging, vol. 10, No. 6, pp. 1-18 (2011).
Uygun et al., "Decellularization and Recellularization of Whole Livers," Journal of Visualized Experiments, vol. 48, pp. 1-4 (2011).
Wang et al., "Lineage Restriction of Human Hepatic Stem Cells to Mature Fates Is Made Efficient by Tissue-Specific Biomatrix Scaffolds," Hepatology, vol. 53, pp. 293-305 (2011).
Anderson et al., "scVEGF Microbubble Ultrasound Contrast Agents: a Novel Probe for Ultrasound Molecular Imaging of Tumor Angiogenesis," Invest Radiol, vol. 45, pp. 1-17 (2010).
Feingold et al., "Quantitative Volumetric Perfusion Mapping of the Microvasculature Using Contrast Ultrasound," Invest Radiol., vol. 45, No. 10, pp. 1-14 (2010).
Gessner et al., "High-Resolution, High-Contrast Ultrasound Imaging Using a Prototype Dual-Frequency Transducer: in Vitro and in Viro Studies," IEEE Transactions on Ultrasonics, Ferroelectrics, and Frequency Control, vol. 57, No. 8, pp. 1772-1781 (2010).
Logeart-Avramoglou et al., "In Vitro and in Vivo Bioluminescent Quantification of Viable Stem Cells in Engineered Constructs," Tissue Eng Part C Methods, vol. 16, No. 3, pp. 447-458 (2010).
Smith et al., "A Comparison of Imaging Methodologies for 3D Tissue Engineering," Microscopy Research and Technique, vol. 73, pp. 1123-1133 (2010).
Uygun et al., "Organ Reengineering Through Development of a Transplantable Recellularized Liver Graft Using Decellularized Liver Matrix," Nature Medicine, vol. 16, pp. 814-820 (2010).
Baptista et al., "Whole Organ Decellularization—A Tool for Bioscaffold Fabrication and Organ Bioengineering," IEEE Eng Med Biol Soc., pp. 6526-6529 (2009).
Behler et al., "ARFI Imaging for Noninvasive Material Characterization of Atherosclerosis Part II: Toward in Vivo Characterization," Ultrasound Med Biol., vol. 35, No. 2, pp. 1-30 (2009).
Catapano et al., "Transport Advances in Disposable Bioreactors for Liver Tissue Engineering," Adv Biochem Engin/Biotechnol., vol. 115, pp. 117-143 (2009).
Kuliszewski et al., "Molecular Imaging of Endothelial Progenitor Cell Engraftment Using Contrast-Enhanced Ultrasound and Targeted Microbubbles," Cardiovasc Res., vol. 83, No. 4, pp. 653-662 (2009).
Liang et al., "Imaging Engineered Tissues Using Structural and Functional Optical Coherence Tomography," Journal of Biophotonics, vol. 2, No. 11, pp. 643-655 (2009).
Terrovitis et al., "Noninvasive Quantification and Optimization of Acute Cell Retention by in Vivo Positron Emission Tomography After Intramyocardial Cardiac-Derived Stem Cell Delivery." J Am Coll Cardiol, vol. 54, No. 17, pp. 1-17 (2009).
Gerlach et al., "Bioartificial Liver Systems: Why, What, Whither?" Regan Med., vol. 3, No. 4, pp. 575-595 (2008).
Hwang et al., "Real-Time in Vivo Monitoring of Viable Stem Cells Implanted on Biocompatible Scaffolds," Eur J Nucl Med Imaging, vol. 35, No. 10, pp. 1887-1898 (2008).
Kim et al., "Non-Invasive Monitoring of Tissue Scaffold Degradation Using Ultrasound Elasticity Imaging," Acta Biomater, vol. 4, No. 4, pp. 1-17 (2008).
Xu et al., "Monitoring Tissue Engineering Using Magnetic Resonance Imaging," Biological Systems Engineering, vol. 106, pp. 515-527 (2008).
Young et al., "Microcomputed Tomography Characterization of Neovascularization in Bone Tissue Engineering Applications," Tissue Engineering: Part B, vol. 14, No. 3, pp. 295-306 (2008).
Kaufmann et al., "Molecular Imaging of Inflammation in Atherosclerosis with Targeting Ultrasound of Vascular Cell Adhesion Molecule-1," vol. 116, No. 3, pp. 276-284 (2007).
De Boer, et al., "Bioluminescent Imaging: Emerging Technology for Non-Invasive Imaging of Bone Tissue Engineering," Biomaterials, vol. 27, No. 9, pp. 1851-1858 (2006).
McGuigan et al., "Vascularized Organoid Engineered by Modular Assembly Enables Blood Perfusion," PNAS, vol. 103, No. 31, pp. 11461-11466 (2006).
Klibanov, "Ligand-Carrying Gas-Filled Microbubbles: Ultrasound Contrast Agents for Targeted Molecular Imaging," Bioconjug Chem, vol. 16, No. 1, pp. 9-17 (2005).
Kruse et al., "A New Imaging Strategy Using Wideband Transient Response of Ultrasound Contrast Agents," IEEE Transactions on Ultrasonics, Ferroelectrics, and Frequency Control, vol. 52, No. 8, pp. 1320-1409 (2005).
Mason et al., "Doppler Optical Coherence Tomography for Measuring Flow in Engineered Tissue," Biosens Bioelectron, vol. 20, No. 3, pp. 414-423 (2004).
Mason et al., "The Potential of Optical Coherence Tomography in the Engineering of Living Tissue," Phys Med Biol, vol. 49, No. 7, pp. 1097-1115 (2004).
Badylak, "The Extracellular Matrix as a Scaffold for Tissue Reconstruction," Cell & Developmental Biology, vol. 13, pp. 377-383 (2002).
Foster et al., "A New Ultrasound Instrument for in Vivo Microimaging of Mice," Ultrasound in Med. & Biol., vol. 28, No. 9, pp. 1165-1172 (2002).
Lindner et al., "Microvascular Rheology of Definity Microbubbles after Intra-Arterial and Intravenous Administration," J Am Soc of Echocardiogr., vol. 15, pp. 396-403 (2002).
Malhi et al., "Early Cell Transplantation in LEC Rats Modeling Wilson's Disease Eliminates Hepatic Copper with Reversal of Liver Disease," Gastroenterology, vol. 122, pp. 438-447 (2002).
Alt et al., "Novel tetravalent and bispecific IgG-like antibody molecules combining single chain diabodies with the immunoglobulin gamma 1 Fc or CH3 region," FEBS Letters, vol. 454, pp. 90-94 (1999).
Gupta et al., "Entry and Integration of Transplanted Hepatocytes in Rat Liver Plates Occur by Disruption of Hepatic Sinusoidal Endothelium," Hepatology, vol. 29, pp. 509-519 (1999).

(56) References Cited

OTHER PUBLICATIONS

Taylor et al., "Regenerating Functional Myocardium: Improved Performance After Skeletal Myoblast Transplantation," Nat Med., vol. 4, pp. 929-933 (1998).
Wei et al., "Quantification of Myocardial Blood Flow with Ultrasound-Induced Destruction of Microbubbles Administered as a Constant Venous Infusion," Circulation, vol. 97, pp. 473-483 (1998).
Reid et al., "Extracellular Matrix Gradients in the Space of Disse: Relevance to Liver Biology," Hepatology, vol. 15, pp. 1198-1203 (1992).
Darlington et al., "Growth and Hepatospecific Gene Expression of Human Hepatoma Cells in a Defined Medium," in Vitro Cell Dev Biol., vol. 23, pp. 349-354 (1987).
Knowles et al., "Human Hepatocellular Carcinoma Cell Lines Secrete the Major Plasma Proteins and Hepatitis B Surface Antigen," Science, vol. 209, pp. 497-499 (1980).
Ultrasonic Transducers Technical Notes pp. 40-50 UT Technotes Olympus 2011 (www.olympus-ims.com).
Notice of Allowance and Fee(s) Due for U.S. Appl. No. 13/393,500 (Aug. 22, 2016).
Applicant-Initiated Interview Summary for U.S. Appl. No. 13/393,500 (Jun. 21, 2016).
Final Office Action for U.S. Appl. No. 13/393,500 (Feb. 24, 2016).
Applicant-Initiated Interview Summary for U.S. Appl. No. 13/393,500 (Nov. 16, 2015).
Non-Final Office Action for U.S. Appl. No. 13/393,500 (Jul. 9, 2015).
Restriction and/or Election Requirement for U.S. Appl. No. 13/393,500 (Jan. 27, 2015).
Allen, "Liposomes—Opportunities in Drug Delivery," Drugs, vol. 54, Suppl. 4, pp. 814 (1997).
Auton et al., "The Force Exerted on a Body in an Inviscid Unsteady Non-Uniform Rotational Flow," J. Fluid Mech., vol. 197, pp. 241-257 (1988).
Bekeredjian et al., "Therapeutic Use of Ultrasound Targeted Microbubble Destruction: a Review of Non-Cardiac Applications," Ultraschall in Med, vol. 27, pp. 134-140 (2006).
Bekeredjian et al., "Ultrasound-targeted Microbubble Destruction Can Repeatedly Direct Highly Specific Plasmid Expression to the Heart," Circulation—Journal of the American Heart Association, vol. 108, pp. 1022-1026 (2003).
Bloch et al., "Targeted Imaging Using Ultrasound Contrast Agents," IEEE Engineering in Medicine and Biology, vol. 23, No. 5, pp. 18-29 (Sep./Oct. 2004).
Borden et al., "Ultrasound Radiation Force Modulates Ligand Availability on Targeted Contrast Agents," Molecular Imaging, vol. 5, No. 3, pp. 139-147 (Jul. 2006).
Borden et al., "Dissolution Behavior of Lipid Monolayer-Coated, Air-Filled Microbubbles: Effect of Lipid Hydrophobic Chain Length," Langmuir, vol. 18, pp. 9225-9233 (2002).
Bouakaz et al., "Contrast Superharmonic Imaging: a Feasability Study," Ultrasound in Med. & Biol., vol. 29, No. 4, pp. 547-553 (2003).
Bouakaz et al., "Super Harmonic Imaging: a New Imaging Technique for Improved Contrast Detection," Ultrasound in Med.& Biol., vol. 28, No. 1, pp. 59-68 (2002).
Brennen, "Cavitation and Bubble Dynamics," Oxford University Press (1995).
Chen et al., "Efficient Gene Delivery to Pancreatic Islets with Ultrasonic Microbubble Destruction Technology," PNAS, vol. 103, No. 22, pp. 8469-8474 (May 30, 2006).
Chen et al., "Multiple Acoustical Matching Layer Design of Ultrasonic Transducer for Medical Application," Jpn. J. Appl. Phys., vol. 41, pp. 6098-6107 (Oct. 2002).
Choi et al., "Spatio-Temporal Analysis of Molecular Delivery Through the Blood-Brain Barrier Using Focused Ultrasound," Physics in Medicine and Biology, vol. 52, pp. 5509-5530 (2007).
Choi et al., "Noninvasive, Transcranial and Localized Opening of the Blood-Brain Barrier Using Focused Ultrasound in Mice," Ultrasound in Medicine and Biology, vol. 33, No. 1, pp. 95-104 (2007).

Chomas et al., "Threshold of Fragmentation for Ultrasonic Contrast Agents," Journal of Biomedical Optics, vol. 6, No. 2, pp. 141-150 (Apr. 2001).
Chomas et al., "Mechanisms of Contrast Agent Destruction," IEEE Transactions Ultrasonics, Ferroelectrics, and Frequency Control, vol. 48, No. 1, pp. 232-248 (Jan. 2001).
Chomas et al., "Optical Observation of Contrast Agent Destruction," Applied Physics Letters, vol. 77, No. 7, pp. 1056-1058 (Aug. 14, 2000).
Chopra et al., "Multifrequency Ultrasound Transducers for Conformal Interstitial Thermal Therapy," IEEE Transactions on Ultrasonics, Ferroelectrics, and Frequency Control, vol. 50, No. 7, pp. 881-889 (Jul. 2003).
Coakley et al., "Ultrasonic Manipulation of Particles and Cells," Bioseparation, vol. 4, pp. 73-83 (1994).
Crowder et al., "Sonic Activation of Molecularly-Targeted Nanoparticles Accelerates Transmembrane Lipid Delivery to Cancer Cells Through Contact-mediated Mechanisms: Implications for Enhanced Local Drug Delivery," Ultrasound in Medicine & Biology, vol. 31, No. 12, pp. 1693-1700 (2005).
Crum, Lawrence A., "Bjerknes Forces on Bubbles in a Stationary Sound Field," The Journal of the Acoustical Society of America, vol. 57, No. 6, Part 1, pp. 1363-1370 (1975).
Crum et al., "The Motion of Bubbles in a Stationary Sound Field," The Journal of the Acoustical Society of America, p. 1411 (1969).
Dayton et al., "Application of Ultrasound to Selectively Localize Nanodroplets for Targeted Imaging and Therapy," Molecular Imaging, vol. 5, No. 3, pp. 1-32 (Jul. 2006).
Dayton et al., "Ultrasonic Analysis of Peptide- and Antibody-Targeted Microbubble Contrast Agents for Molecular Imaging of αvβ3-expressing Cells," Molecular Imaging, vol. 3, No. 2, pp. 1-18 (Apr. 2004).
Dayton et al., "Targeted Imaging Using Ultrasound," Journal of Magnetic Resonance Imaging, vol. 16, pp. 362-377 (2002).
Dayton et al., "The Magnitude of Radiation Force on Ultrasound Contrast Agents," The Journal of the Acoustical Society of America, vol. 112, No. 5, Part 1, pp. 2183-2192 (2002).
Dayton et al., "Optical and Acoustical Dynamics of Microbubble Contrast Agents Inside Neutrophils," Biophysical Journal, vol. 80, pp. 1547-1556 (Mar. 2001).
Dayton et al., "Acoustic Radiation Force in Vivo: a Mechanism to Assist Targeting of Microbubbles," Ultrasound in Med. and Biol. Vol. 25, No. 8, pp. 1195-1201 (1999).
Dayton et al., "Optical and Acoustical Observations of the Effects of Ultrasound on Contrast Agents," IEEE Transactions on Ultrasonics, Ferroelectrics, and Frequency Control, vol. 46, No. 1, pp. 220-232 (Jan. 1999).
Dayton et al., "A Preliminary Evaluation of the Effects of Primary and Secondary Radiation Forces on Acoustic Contrast Agents," IEEE Transactions on Ultrasonics, Ferroelectrics, and Frequency Control, vol. 44, No. 6, pp. 1264-1277 (Nov. 1997).
Dayton et al., "Action of Microbubbles When Insonified: Experimental Evidence," IEEE Ultrasonics Symposium, vol. 2, pp. 1131-1134 (1996).
Deng et al., "Ultrasound-Induced Cell Membrane Porosity," Ultrasound in Medicine & Biology, vol. 30, No. 4, pp. 519-526 (2004).
Desilets et al., "Design of Efficient Broad-Band Piezoelectric Transducers," IEEE Transactions on Sonics and Ultrasonics, vol. SU-25, No. 3, pp. 115-125 (May 1978).
Dromi et al., "Pulsed-High Intensity Focused Ultrasound and Low Temperature Sensitive Liposomes for Enhanced Targeted Drug Delivery and Antitumor Effect," Clinical Cancer Research, vol. 13, pp. 2722-2727 (2007).
Ellegala et al., "Imaging Tumor Angiogenesis with Contrast Ultrasound and Microbubbles Targeted to αvβ3," Circulation, Journal of the American Heart Association, vol. 108 pp. 336-341 (2003).
Ferrara, "Driving Delivery Vehicles with Ultrasound," Advanced Drug Delivery Reviews, vol. 60, No. 10, pp. 1-9 (Jun. 30, 2008).
Gessner et al., "High-Resolution, High-Contrast Ultrasound Imaging Using a Prototype Dual-Frequency Transducer: in Vitro and in Vivo Studies," IEEE Transactions on Ultrasonics, Ferroelectrics, and Frequency Control, vol. 57. No. 8. pp. 1772-1781 (Aug. 2010).

(56) References Cited

OTHER PUBLICATIONS

Gessner et al., "Radiation Force-Enhanced Targeted Imaging and Near Real-time Molecular Imaging Using a Dual-Frequency High-resolution Transducer: In-vitro and In-vivo Results," Proceedings of the 2009 IEEE Ultrasonics Symposium, in Press, pp. 1-4, (2009).
Goll, "Design of Broad-Band Fluid-Loaded Ultrasonic Transducers," IEEE Transactions on Sonics and Ultrasonics, vol. SU-26, No. 6, pp. 385-393 (Nov. 1979).
Groschl, "Ultrasonic Separation of Suspended Particles—Part I: Fundamentals," Acustica, vol. 84, pp. 432-447 (1998).
Hynynen et al., "Local and Reversible Blood-Brain Barrier Disruption by Noninvasive Focused Ultrasound at Frequencies Suitable for Trans-skull Sonications," NeuroImage, vol. 24, pp. 12-20 (2005).
Jayaweera et al., "In Vivo Myocardial Kinetics of Air-Filled Albumin Microbubbles During Myocardial Contrast Echocardiography. Comparison with Radiolabeled Red Blood Cells," Circulation Research—The Journal of the American Heart Association, vol. 74. No. 6. pp. 1157-1165 (1994).
Jones et al., "Prospective Thermal Dosimetry: the Key to Hyperthermia's Future," International Journal of Hyperthermia, vol. 22, No. 3, pp. 247-253 (May 2006).
Klibanov et al., "Targeting and Ultrasound Imaging of Microbubble-based Contrast Agents," Magnetic Resonance Materials in Physics, Biology, and Medicine, vol. 8, pp. 177-184 (1999).
Klibanov et al., "Targeting of Ultrasound Contrast Material. An in vitro Feasibility Study," Acta Radiologica, Supplement 412, pp. 113-120 (1997).
Krishnan et al., "Inertial lift on a Moving Sphere in Contact with a Plane Wall in a Shear Flow," Phys. Fluids, vol. 7, No. 11, pp. 2538-2545 (1995).
Kruse et al., "Spatial and Temporal-Controlled Tissue Heating on a Modified Clinical Ultrasound Scanner for Generating Mild Hyperthermia in Tumors," IEEE Transactions on Biomedical Engineering, vol. 57, No. 1, pp. 155-166 (Jan. 2010).
Kruse et al., "A New Imaging Strategy Using Wideband Transient Response of Ultrasound Contrast Agents," IEEE Transactions on Ultrasonics, Ferroelectrics and Frequency Control, vol. 52, No. 8, pp. 1-22 (Aug. 2005).
Lamberti et al., "A New Approach for the Design of Ultrasono-Therapy Transducers," IEEE Transactions on Ultrasonics, Ferroelectrics, and Frequency Control, vol. 44, No. 1, pp. 77-84 (Jan. 1997).
Lanza et al., "Targeted Ultrasonic Contrast Agents for Molecular Imaging and Therapy," Current Problems in Cardiology, pp. 625-653 (Dec. 2003).
Lanza et al., "High-Frequency Ultrasonic Detection of Thrombi with a Targeted Contrast System," Ultrasound in Med. & Biol., vol. 23, No. 6, pp. 863-870 (1997).
Lanza et al., "A Novel Site—Targeted Ultrasonic Contrast Agent with Broad Biomedical Application," Circulation, vol. 94. pp. 1-9 (1996).
Leong-Poi et al., "Noninvasive Assessment of Angiogenesis by Ultrasound and Microbubbles Targeted to αv-Integrins," Circulation—Journal of the American Heart Association, vol. 107, pp. 455-460 (2003).
Lindner, "Microbubbles in Medical Imaging: Current Applications and Future Directions," Nature Reviews—Drug Discovery, vol. 3, pp. 527-532 (Jun. 2004).
Lindner, "Evolving Applications for Contrast Ultrasound," the American Journal of Cardiology, vol. 90, No. 10A, pp. 72J-80J (2002).
Lindner et al., "Assessment of Resting Perfusion with Myocardial Contrast Echocardiography: Theoretical and Practical Considerations," the American Heart Journal, vol. 139, No. 2, Part 1, pp. 231-240 (2000).
Linker et al., "In Vivo Molecular Imaging of Adhesion Molecules in Experimental Autoimmune Encephalomyelitis (EAE)," Journal of Autoimmunity, vol. 25, pp. 199-205 (2005).

Lockwood et al., "Modeling and Optimization of High-Frequency Ultrasound Transducers," IEEE Transactions on Ultrasonics, Ferroelectrics, and Frequency Control, vol. 41, No. 2, pp. 225-230 (Mar. 1994).
Lum et al., "Ultrasound Radiation Force Enables Targeted Deposition of Model Drug Carriers Loaded on Microbubbles," Journal of Controlled Release, vol. 111, No. 1-2, pp. 1-15 (Mar. 2006).
Macedo et al., "Acoustic Effects on Gas Bubbles in the Flows of Viscous Fluids and Whole Blood," the Journal of the Acoustical Society of America, vol. 53, No. 5, pp. 1327-1335 (1973).
McKeighen, "Design Guidelines for Medical Ultrasonic Arrays," SPIE, vol. 3341, pp. 1-18 (1998).
Meyer et al., "Freestream Nuclei and Traveling-Bubble Cavitation," Transactions of the ASME, vol. 114, pp. 672-679 (Dec. 1992).
Miller et al., "Lysis and Sonoporation of Epidermoid and Phagocytic Monolayer Cells by Diagnostic Ultrasound Activation of Contrast Agent Gas Bodies," Ultrasound in Medicine and Biology, vol. 27, No. 8, pp. 1107-1113 (2001).
Miller et al., "Sonoporation of Monolayer Cells by Diagnostic Ultrasound Activation of Contrast-Agent Gas Bodies," Ultrasound in Medicine and Biology, vol. 26, No. 4, pp. 661-667 (2000).
Miller et al., "Sonoporation of Cultured Cells in the Rotating Tube Exposure System," Ultrasound in Medicine and Biology, vol. 25, No. 1, pp. 143-449 (1999).
Mitragotri, "Healing Sound: the Use of Ultrasound in Drug Delivery and Other Theraputic Applications," Nature Reviews, Drug Discovery, vol. 4, pp. 255-260 (Mar. 2005).
Morgan, "Experimental and Theoretical Evaluation of Ultrasonic Contrast Agent Behavior," Dissertation, University of Virginia, (Jan. 2001).
Morgan et al., "Experimental and Theoretical Evaluation of Microbubble Behavior: Effect of Transmitted Phase and Bubble Size," IEEE Transactions on Ultrasonics, Ferroelectrics, and Frequency Control, vol. 47, No. 6, pp. 1494-1509 (Nov. 2000).
Morgan et al., "Changes in the Echoes from Ultrasonic Contrast Agents with Imaging Parameters," IEEE Transactions on Ultrasonics, Ferroelectrics, and Frequency Control, vol. 45, No. 6, pp. 1537-1548 (Nov. 1998).
Mulvagh et al., "Contrast Echocardiography: Current and Future Applications," Journal of the American Society of Echocardiography, vol. 13, No. 4, pp. 331-342 (Apr. 2000).
Nyborg, "Solutions of the Bio-Heat Transfer Equation," Physics in Medicine and Biology, vol. 33, No. 7, pp. 785-792 (1988).
Oakley, "Calculation of Ultrasonic Transducer Signal-to-Noise Rations Using the KLM Model," IEEE Transactions on Ultrasonics, Ferroelectrics, and Frequency Control, vol. 44, No. 5, pp. 1018-1026 (Sep. 1997).
Pan et al., "Study of Sonoporation Dynamics Affected by Ultrasound Duty Cycle," Ultrasound in Medicine and Biology, vol. 31, No. 6, pp. 849-856 (2005).
Pan et al., "Sonoporation of Cells for Drug and Gene Delivery," Conf Proc IEEE Eng Med Biol Soc, vol. 5, pp. 3531-3534 (2004).
Park et al., "Unsteady Forces on Spherical Bubbles," Experimnets in Fluids, vol. 19, pp. 167-172 (1995).
Patil et al., "Particle Diameter Influences Adhesion Under Flow," Biophysical Journal, vol. 80, pp. 1733-1743 (Apr. 2001).
Pitt et al., "Ultrasonic Drug Delivery—a General Review," Expert Opinion on Drug Delivery, vol. 1, pp. 1-32 (Nov. 2004).
Plesset et al., "Bubble Dynamics and Cavitation," Annu. Rev. Fluid Mech., vol. 9, pp. 145-185 (1977).
Price et al., "Delivery of Colloidal Particles and Red Blood Cells to Tissue Through Microvessel Ruptures Created by Targeted Microbubble Destruction with Ultrasound," Journal of the American Heart Association, vol. 98, pp. 1264-1267 (Sep. 29, 1998).
Prosperetti, "Bubble Phenomena in Sound Fields: Part Two," Ultrasonics, vol. 22, pp. 115-124 (May 1984).
Reddy et al., "Coupled Dynamics of Translation and Collapse of Acoustically Driven Microbubbles," J. Acoust. Soc. Am., vol. 112, No. 4, pp. 1346-1352 (Oct. 2002).
Reinhardt et al., "Ultrasound Derived Imaging and Quantification of Cell Adhesion Molecules in Experimental Autoimmune Encephalomyelitis (EAE) by Sensitive Particle Acoustic Quantification (SPAQ)," NeuroImage, vol. 27, pp. 267-278 (2005).

(56) References Cited

OTHER PUBLICATIONS

Rychak et al., "Enhanced Targeting of Ultrasound Contrast Agents Using Acoustic Radiation Force," Ultrasound in Medicine and Biology, vol. 33, No. 7, pp. 1132-1139 (Jul. 2007).
Rychak et al., "Acoustic Radiation Force Enhances Targeted Delivery of Ultrasound Contrast Microbubbles: in Vitro Verification," IEEE Transactions on Ultrasonics, Ferroelectrices, and Frequency Control, vol. 52, No. 3, pp. 421-433 (Mar. 2005).
Schroeder et al., "Ultrasound Triggered Release of Cisplatin from Liposomes in Murine Tumors," Journal of Controlled Release, vol. 137, pp. 63-68 (2009).
Schumann et al., "Targeted-Microbubble Binding Selectively to GPllb llla Receptors of Platelet Thrombi," Investigative Radiology, vol. 37, No. 11, pp. 587-593 (Nov. 2002).
Shortencarier et al., "A Method for Radiation-Force Localized Drug Delivery Using Gas-Filled Liposheres", IEEE Transactions on Ultrasonics, Ferroelectrices and Frequency Control, vol. 51, No. 7, pp. 822-831 (Jul. 2004).
Stephens et al., "Efficient Array Design for Sonotherapy," Phys Med Biol., vol. 53, No. 14, pp. 1-42 (Jul. 21, 2008).
Stephens et al., "Multi-frequency Array Development for Drug Delivery Therapies: Characterization and First Use of a Triple Row Ultrasound Probe," IEEE Ultrasonics Symposium, pp. 66-69 (2006).
Stieger et al., "Enhancement of Vasular Permeability with Low-Frequency Contrast-Enhanced Ultrasound in the Chorioallantoic Membrane Model," Radiology, vol. 243, No. 1, pp. 112-121 (Apr. 2007).
Takeuchi et al., "Enhanced Visualization of Intravascular and Left Atrial Appendage Thrombus with the Use of a Thrombus-Targeting Ultrasonographic Contrast Agent (MRX-408A1): in Vivo Experimental Echocardioraphic Studies," Journal of the American Society of Echocardiography, vol. 12, No. 12, pp. 1015-1021 (Dec. 1999).
Tartis et al., "Therapeutic Effects of Paclitaxel-Containing Ultrasound Contrast Agents," Ultrasound in Medicine and Biology, vol. 32, No. 11, pp. 1771-1780 (2006).
Tortoli et al., "Unexpected Doppler Effects from Microbubbles Moving Through an Ultrasound Beam," IEEE Ultrasonics Symposium, vol. 2, pp. 1729-1732 (1999).
Ueda et al., "Acoustic Cavitation as an Enhancing Mechanism of Low-Frequency Sonophoresis for Transdermal Drug Delivery," Biol. Pharm. Bull, vol. 32, No. 5, pp. 916-920 (2009).
Unger et al., "Therapeutic Applications of Lipid-Coated Microbubbles," Advanced Drug Delivery Reviews, vol. 56, pp. 1291-1314 (2004).
Unger et al., "Therapeutic Applications of Microbubbles," European Journal of Radiology, vol. 42, pp. 160-688 (2002).
Unger et al., "Local Drug and Gene Delivery Through Microbubbles," Progress in Cardiovascular Diseases, vol. 44, No. 1, pp. 45-54 (Jul./Aug. 2001).
Unger et al., "In Vitro Studies of a New Thrombus-Specific Ultrasound Contrast Agent," Am J Cardiol, vol. 81, No. 12A, pp. 58G-61G (1998).
Van Wamel et al., "Vibrating Microbubbles Poking Individual Cells: Drug Transfer Into Cells Via Sonoporation," Journal of Controlled Release, vol. 112, pp. 149-155 (2006).
Villanueva et al., "Microbubbles Targeted to Intracellular Adhesion Molecule-1 Bind to Activated Coronary Artery Endothelial Cells," Circulation, vol. 98, pp. 1-6 (1998).
Vorkurka, "Comparison of Rayleigh's, Herring's, and Gilmore Models of Gas Bubbles," Acustica, vol. 59, pp. 214-219 (1986).
Ward et al., "Experimental Study of the Effects of Optison Concentration on Sonoporation in Vitro," Ultrasound in Medicine & Biology, vol. 26, No. 7, pp. 1169-1175 (May 2, 2000).
Watanabe et al., "Translational and Radical Motions of a Bubble in an Acoustic Standing Wave Field," Phys. Fluids A, vol. 5, No. 11, pp. 2682-2688 (Nov. 1993).
Wei et al., "Recent Advances in Myocardial Contrast Echoardiography," Curr. Opin. Cardiol., vol. 12, pp. 539-546 (1997).
Whitworth, "Discussion of One-D Piezoelectric Transducer Models With Loss," IEEE Transactions on Ultrasonics, Ferroelectrics and Frequency Control, vol. 48, No. 3, pp. 844-846 (May 2001).
Wright et al., "Evaluation of New Thrombus-Specific Ultrasound Contrast Agent," Acad Radiol, vol. 5 (supp 1), pp. S240-S242 (1998).
Wu et al., "PSPICE Approach for Designing the Ultrasonic Piezoelectric Transducer for Medical Diagnostic Applications," Sensors and Actuators, vol. 75, pp. 186-198 (1999).
Yasuda et al., "Using Acoustic Radiation Force as a Concentration Method for Erythrocytes," J. Acoust. Soc. Am., vol. 102, No. 1, pp. 642-645 (Jul. 1997).
Zhao et al., "Selective Imaging of Adherent Targeted Ultrasound Contrast Agents," Physics in Medicine and Biology, vol. 52, pp. 2055-2072 (2007).
Zhao et al., "Radiation-Force Assisted Targeting Facilitates Ultrasonic Molecular Imaging," Molecular Imaging, vol. 3, No. 3, pp. 135-148 (Jul. 2004).
Zheng et al., "A Novel Sensitive Targeted Imaging Technique for Ultrasonic Molecular Imaging," IEEE 2007 Ultrasonics Symposium, pp. 957-960 (2007).
Zipparo, "Mid- to High-Power Ultrasound Imaging Arrays—from ARFI to HIFU," IEEE 2003 Ultrasonics Symposium; Honolulu, Hawaii, pp. 684-688 (2003).

* cited by examiner

FIG. 8A  FIG. 8B
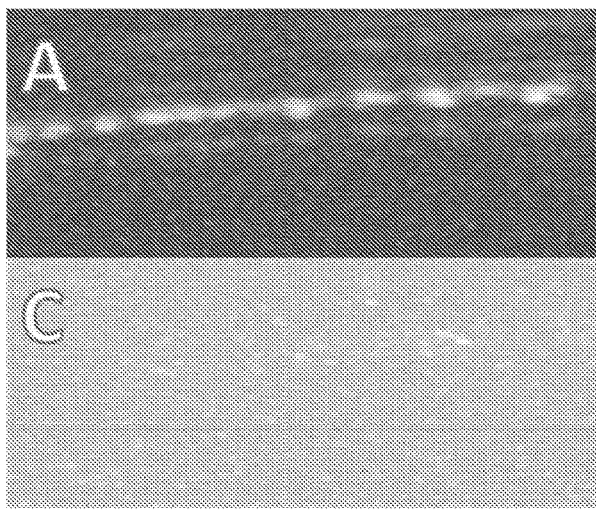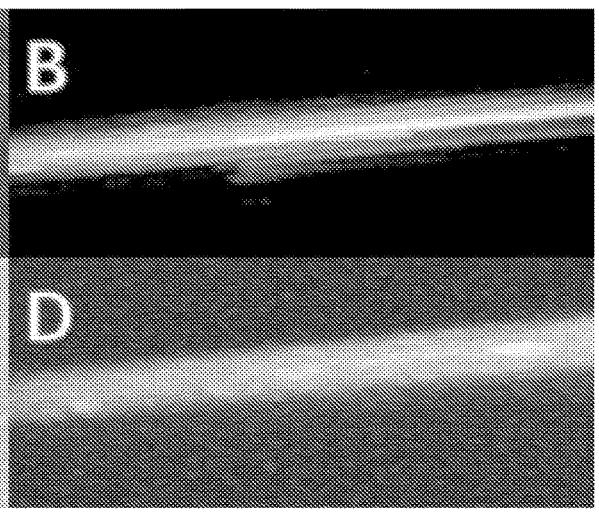
FIG. 8C  FIG. 8D

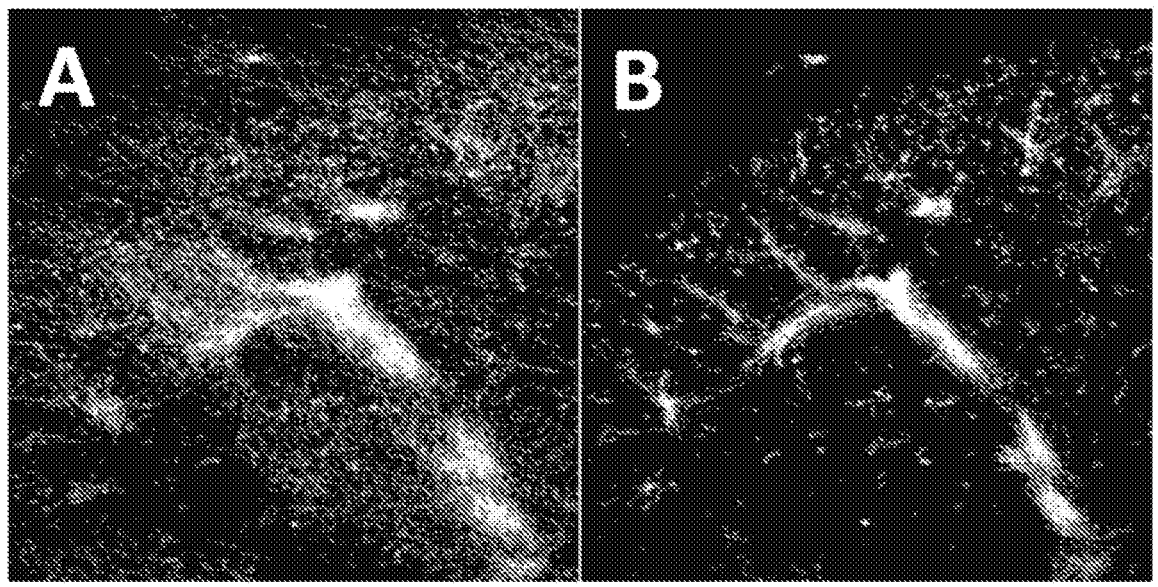
*FIG. 12A*     *FIG. 12B*

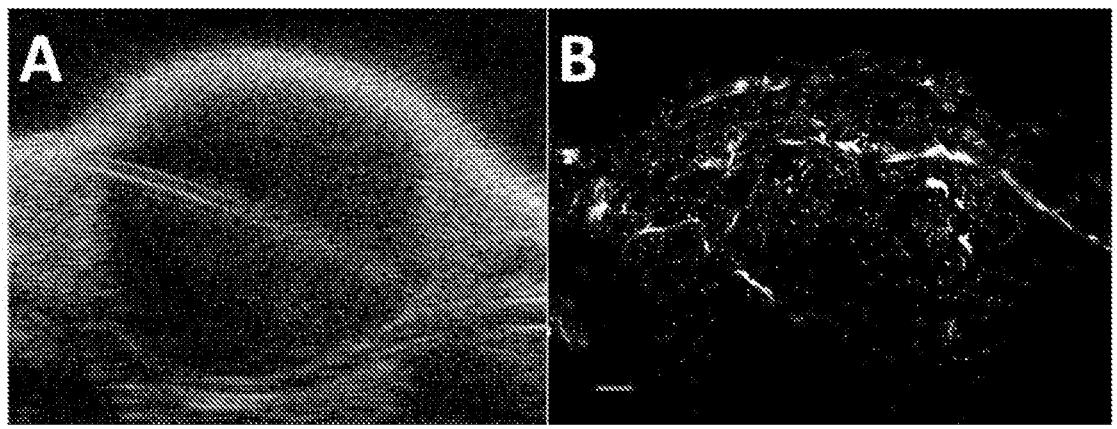
*FIG. 15A*  *FIG. 15B*

METHODS, SYSTEMS, AND COMPUTER READABLE MEDIA FOR GENERATING SUPER-RESOLUTION IMAGES OF MICROVASCULATURE USING ULTRASOUND

PRIORITY APPLICATION

This application claims the priority benefit of U.S. Provisional Patent Application Ser. No. 62/846,133, filed May 10, 2019, the disclosure of which is incorporated herein by reference in its entirety.

GOVERNMENT INTEREST

This invention was made with government support under Grant Numbers CA220681 and CA189479 awarded by the National Institutes of Health. The government has certain rights in the invention.

TECHNICAL FIELD

The subject matter described herein relates to generating images of the microvasculature. More particularly, the subject matter described herein relates to methods, systems, and computer readable media for generating images of the microvasculature using ultrasound.

BACKGROUND

Traditional ultrasound imaging, with or without contrast agents, is 'diffraction limited'. This means that the best case resolution of the imaging system is dictated by the frequency of the ultrasound wave, the pulse length, and the beam diameter. The beam diameter is also a function of the aperture (aperture is the size—i.e., the diameter, if the transducer is circular) of the transducer and the distance of the transducer to the target (focal length). These constraints are for circular transducers, but the physics is similar for rectangular transducers. That means, for example, that the best case axial resolution is one half of the pulse length, i.e., the spatial extent of the acoustic pulse. For clinical ultrasound systems that operate between 2-10 MHz, for example, the best resolution is on the order of a few hundred microns. If you have two 50 micron vessels 50 microns apart, they will be blurred into one vessel.

Accordingly, in light of these difficulties, there exists a need for improved methods, systems and computer readable media for generating images of the microvasculature using ultrasound.

SUMMARY

A method for producing an image of at least one vessel with ultrasound includes administering a contrast agent particle into the at least one vessel, and delivering an ultrasound pulse having a first frequency range to the at least one vessel. The method further includes detecting ultrasound energy scattered from the contrast agent particle at a second frequency range that is different from the first frequency range, converting the scattered ultrasound energy into an electronic radio frequency signal, and using an algorithm to determine a spatial location of the contrast agent particle based on extraction of a specific feature of the radio frequency signal. The method further includes generating an image by displaying a marker of the spatial location of the contrast agent particle with a resolution that is finer than a pulse length of the ultrasound pulse and repeating the detecting, converting, using, and generating for a plurality of contrast agent particles until sufficient markers have been accumulated to reconstruct a pattern of the at least one vessel; wherein the pattern is an image of the at least one vessel.

According to one aspect of the subject matter described herein, a resolution of the image is at least twice as fine as the pulse length of the ultrasound pulse.

According to another aspect of the subject matter described herein, the at least one vessel comprises a blood vessel, a lymphatic vessel, or part of a venous or capillary network in a human body.

According to yet another aspect of the subject matter described herein, endothelial cells within the at least one vessel express a biomarker which causes the contrast agent particles to adhere to a wall of the at least one vessel.

According to yet another aspect of the subject matter described herein, the particles are stationary within the at least one vessel.

According to yet another aspect of the subject matter described herein, the pattern is an image of contrast agent particle distribution within vessels of tissue, an organ, or a tumor.

According to yet another aspect of the subject matter described herein, the contrast agent particle is first detected by detecting ultrasound energy scattered from the contrast agent particle after exciting the contrast agent particle with ultrasound energy in the first frequency range with a single pulse.

According to yet another aspect of the subject matter described herein, the mean or the median of the second frequency range detected is at least double or at least triple the mean or the median of the first frequency range.

According to yet another aspect of the subject matter described herein, detecting the ultrasound energy scattered from the contrast agent particle utilizes transmitting and receiving ultrasound transducers having at least one of non-overlapping −6 dB bandwidths and non-overlapping −12 dB bandwidths.

According to yet another aspect of the subject matter described herein, the contrast agent particles include at least one of microbubbles and nanobubbles.

According to yet another aspect of the subject matter described herein, the contrast agent particles include phase-change agents each comprising a liquid perfluorocarbon core prior to ultrasound exposure.

According to yet another aspect of the subject matter described herein, the algorithm includes high pass filtering followed by a thresholding operation.

According to yet another aspect of the subject matter described herein, the algorithm includes using a centroid of the radio frequency signal to estimate a location of the contrast agent particle.

According to yet another aspect of the subject matter described herein, the algorithm includes using an onset of the radio frequency signal to estimate the location of the contrast agent particle.

According to yet another aspect of the subject matter described herein, the algorithm allows calculation of a velocity and a direction of the contrast agent particle.

According to yet another aspect of the subject matter described herein, the algorithm determines the spatial location of the contrast agent particle without using a singular value decomposition filter.

According to another aspect of the subject matter described herein, the ultrasound pulse having a first frequency range is transmitted with zero phase delay across a plurality of elements of a transmitting ultrasound transducer to emit a plane wave into the at least one vessel.

According to yet another aspect of the subject matter described herein, the system of claim 20 wherein the first frequency range is between 0.5 and 5 MHz, and the second frequency range is between 5 and 50 MHz.

According to yet another aspect of the subject matter described herein, a system for producing an image of at least one vessel using ultrasound is provided. The system includes at least one ultrasound transducer for delivering an ultrasound pulse having a first frequency range to at least one vessel infused with a contrast agent particle, for detecting ultrasound energy scattered from the contrast agent particle at a second frequency range that is different from the first frequency range, and for converting the scattered ultrasound energy into an electronic radio frequency signal. The system further includes a super-resolution processor for using an algorithm to determine a spatial location of the contrast agent particle based on extraction of a specific feature of the radio frequency signal, generating an image by displaying a marker of the spatial location of the contrast agent particle with a resolution that is finer than a pulse length of the ultrasound pulse, and repeating the detecting, converting, using, and generating for a plurality of contrast agent particles until sufficient markers have been accumulated to reconstruct a pattern of the at least one vessel; wherein the pattern is an image of the at least one vessel.

According to yet another aspect of the subject matter described herein, a non-transitory computer readable medium having stored thereon executable instructions that when executed by a processor of a computer control the computer to perform steps is provided. The steps include controlling at least one ultrasound transducer for delivering an ultrasound pulse having a first frequency range to at least one vessel infused with a contrast agent, detecting ultrasound energy scattered from the contrast agent particle at a second frequency range that is different from the first frequency range, and converting the scattered ultrasound energy into an electronic radio frequency signal. The steps further include using an algorithm to determine a spatial location of the contrast agent particle based on extraction of a specific feature of the radio frequency signal. The steps further include generating an image by displaying a marker of the spatial location of the contrast agent particle with a resolution that is finer than a pulse length of the ultrasound pulse. The steps further include repeating the detecting, converting, using, and generating for a plurality of contrast agent particles until sufficient markers have been accumulated to reconstruct a pattern of the at least one vessel; wherein the pattern is an image of the at least one vessel.

The subject matter described herein may be implemented in hardware, software, firmware, or any combination thereof. As such, the terms "function," "node," or "module" as used herein refer to hardware, which may also include software and/or firmware components, for implementing the feature being described. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

The subject matter described herein will now be explained with reference to the accompanying drawings of which:

FIGS. 4A and 4B are reproduced from Cherin et al. with permission [26];

FIG. 5A illustrates an imaging sequence used for this study. Chunks of 100 DF frames collected at a frame rate of 500 Hz are separated by b-mode frames for motion tracking. RF data are saved after 1000 DF frames. In FIG. 5B, speckle tracking is performed between a manually selected reference frame and each b-mode frame to estimate the non-rigid deformation of the kidney during imaging. In FIG. 5C, DF images are processed using a threshold and peak detector to localize MBs. These positions are then corrected according to the displacements estimated from speckle tracking or thrown out if the parent b-mode patch is not well correlated with the reference patch;

FIG. 6A is a SHI-ULM image generated from 25000 frames. FIG. 6B is a maximum intensity projection (MIP) of the super harmonic imaging (SHI) frames used to generate the image in FIG. 6A. FIG. 6C is a graph of average profiles within the regions of interest from FIGS. 6A and 6B. In FIG. 6C, the inner (narrower) peak is for SHI-ULM. The outer or wider profile peak is for dual-frequency MIP. The full width at half maximum (FWHM) values of the acoustic angiography (AA) and SHI-ULM profiles are 113 and 44 μm, respectively; demonstrating that SHI-ULM can resolve the true tube diameter, even though superharmonic imaging cannot.

FIG. 7A is a direction map with flow direction indicated by the color wheel. FIG. 7B is a map of the average speed for each pixel.

FIGS. 8A-8D are MIPs for singular value decomposition (SVD)-filtered and superharmonic images of a 200-μm tube in different flow regimes. All images are displayed on a 25-dB dynamic range for comparison. FIG. 8A is a MIP of superharmonic images collected at 0.25 μL/min. FIG. 8B is a MIP of superharmonic images collected at 15.0 μL/min. FIG. 8C is a MIP of SVD-filtered images collected at 0.25 μL/min. FIG. 8D is a MIP of SVD-filtered images collected at 15.0 μL/min;

FIG. 10A is a b-mode scan of the kidney used as a reference for motion correction. FIG. 10B is a MIP of superharmonic images used to generate the SHI-ULM image (frames with motion discarded). FIG. 10C is a SHI-ULM image generated from 25000 frames with motion correction applied;

FIGS. 11A-11C illustrate example vessels cropped from SHI-ULM images.

FIGS. 12A and 12B illustrate a comparison of SHI-ULM with and without motion correction based on sparsely interleaved b-mode frames. FIG. 12A illustrates rodent kidney vessels are smeared out by respiratory and cardiac motion artifacts. FIG. 12B illustrates fine detail of the vessel structure is recovered by a combination of removal of decorrelated frames and using speckle tracking to estimate nonrigid displacements;

FIG. 13A illustrates the average direction of MBs for the SHI-ULM image in FIG. 10C. FIG. 13B illustrated the magnitude of the velocity for the same data set;

FIGS. 15A and 15B illustrate examples of super-resolution molecular imaging in-vivo in a rodent tumor model. The scale bar on the lower left hand corner of FIG. 15B is 1 mm. FIG. 15A is a b-mode image from the center slice of the tumor. FIG. 15B is a SHI-ULM vascular image shown in grayscale overlaid with localizations of VEGFR2-targeted microbubbles (small dots in image). The ULM image is a maximum intensity projection from 5 slices spaced by 1 mm.

DETAILED DESCRIPTION

Figure 1:
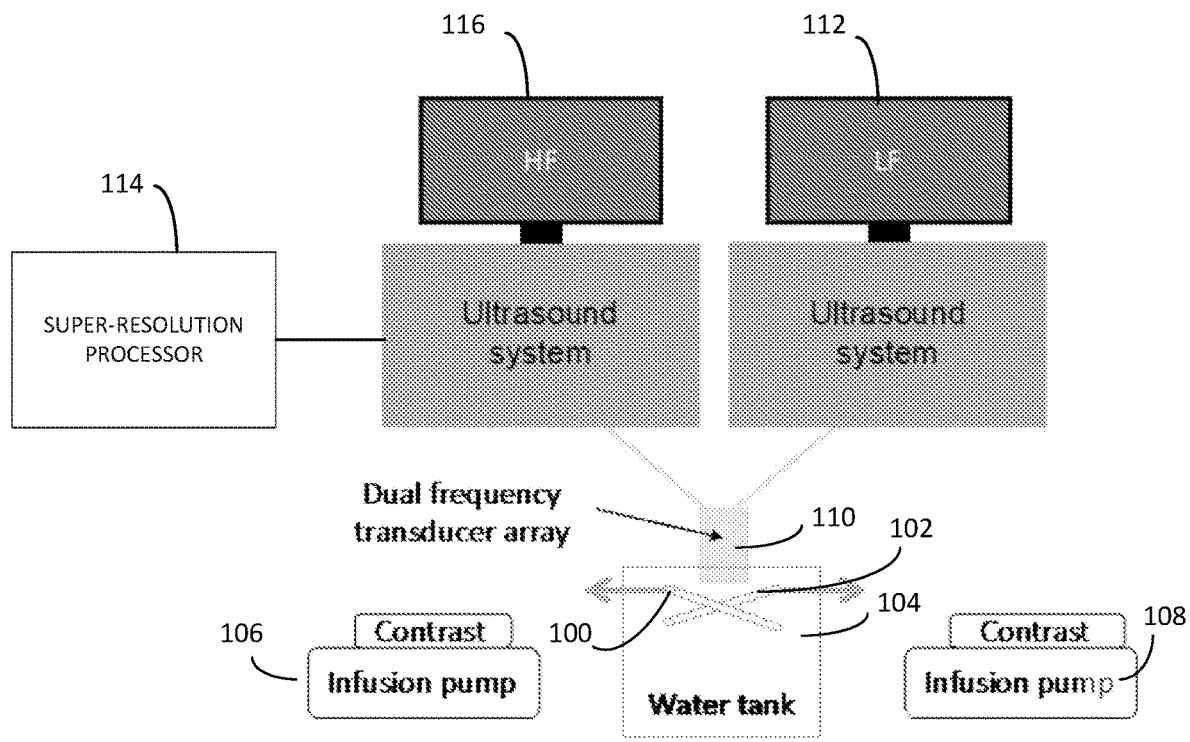
FIG. 1 is a block diagram of a test setup for evaluating the imaging capabilities of dual-frequency mode microvasculature imaging.

In order to address the resolution issues with diffraction limited ultrasound, the subject matter described herein utilizes a technique called ultrasound localization microscopy, or super-resolution imaging, which allows you to image vessels below the diffraction limit. Microbubble contrast agents are injected into vessels, detected, and then used to create images of vessels with resolution as small as 20 microns or smaller, whereas diffraction limited ultrasound resolution would be approximately 10× worse. However, these techniques involve detecting the presence of microbubbles either by their movement (usually through a singular value decomposition filter or similar technique). The subject matter described herein includes improvements to super-resolution imaging by providing a mechanism for detecting these microbubbles using a difference in the frequency of ultrasound that the microbubbles scatter, compared to the frequency of ultrasound that is sent into the sample volume. Specifically, this frequency difference is quite large, ideally receiving above the third harmonic of the transmitted frequency. In one exemplary implementation, we transmit with a 2 MHz transmitter and receive with a 20 MHz receiver. Because we are using a very wideband transducer, and we are listening to frequencies of ultrasound far above what is transmitted, the bubbles can be detected with good sensitivity and there is a very low noise background from tissue, which otherwise confounds bubble detection. The result is that the bubbles do not need to be moving to be detected, or they can be detected even when moving very slowly. After this detection of bubbles using the frequency difference, we can perform some of the analysis steps of super-resolution imaging to make images of vessels with a resolution finer than that using diffraction limited ultrasound imaging.

The following steps illustrate an example of data acquisition for producing an image of a vessel using ultrasound.
1.) A contrast agent is administered to a subject, preferably into a blood vessel or lymphatic vessel. The subject may be a human patient, a non-human animal, or in an in-vitro vessel. The contrast agent may be a microbubble, a nanobubble, or a phase change liquid perfluorocarbon nanodroplet.
2.) A low-frequency pulse generated by a wide-bandwidth ultrasonic transducer is transmitted into the subject, causing the contrast agent to change diameter, typically in an oscillatory fashion. As the contrast agent oscillates, the contrast agent scatters ultrasound of many different frequencies. In one implementation, an ultrasound transducer with separate transmit and receive arrays or elements which provide a very wide bandwidth can be used to transmit the ultrasound pulse into the subject. In an alternate implementation, a CMUT (capacitive micromachined ultrasonic transducer), which has a wide bandwidth, may be used to transmit and detect the ultrasound energy.
3.) The echoes scattered by the contrast agent are detected by an ultrasound transducer (either the transmitting transducer or a separate transducer).
4.) One aspect of the subject matter described herein is the combination of ultrasound imaging where the frequency content of the scattered echoes received is higher than that of the low-frequency pulse transmitted into the subject with super-resolution imaging. One example of an ultrasound imaging technique suitable for use with the subject matter described herein is described in U.S. Pat. No. 9,553,769, the disclosure of which is incorporated herein by reference in its entirety.
5.) The above process is repeated successive times to gather many hundreds of samples of the same volume.

Once the scattered ultrasound energy measurements are collected, the measurements are used to generate a super-resolution image of the vessel. The following are exemplary steps for vessel image formation.
1.) Radio frequency (RF) echo data are filtered to isolate the contrast agent acoustic response from that of the tissue. Typically, a high-pass filter would be applied to the received echoes, so that only the echoes returning from the contrast agent, and not any low frequency echoes scattered from tissue, would be preserved.

2.) Dynamic receive beamforming is used to generate a stack of b-mode images from the RF data.

3.) A threshold is applied to each b-mode image. Each pixel in the resulting image is equal to the original image value if the reference pixel value is greater than or equal to the threshold, and zero otherwise.

4.) A mechanism is used to estimate the location of the contrast agent. One mechanism would be to use a Gaussian kernel with a root mean squared (RMS) width equal to that of the point-spread function (PSF) of the imaging system, which is convolved over the stack of images generated in step 3. Contrast agent centroids are estimated using either center-of-mass for each connected component or by using a simple peak detection (slightly faster).

5.) In one implementation, particle tracking is performed on each stack of centroid images and line segments are drawn between particles that appear in adjacent frames.

6.) Contrast agent locations from the centroid (step 4) or line segments (step 5) are accumulated over many frames to generate a super-resolved image of the vessels in the sample volume.

Additional examples of super-resolution processing techniques suitable for use with the subject matter described herein are provided in Couture, et al., Ultrasound Location Microscopy and Super Resolution: A State of the Art, IEEE Transaction on Ultrasonics, Ferroelectrics, and Frequency Control, Vol. 65, No. 8, August 2018 and Christensen-Jeffries et al., Microbubble Axial Localization Errors in Ultrasound Super-Resolution Imaging, the disclosures of which are incorporated herein by reference in their entireties.

FIG. 1 is a block diagram of a test system used to evaluate the vessel imaging methodology described herein. Referring to FIG. 1, simulated vessels 100 and 102 are suspended in a water tank 104. Each simulated vessel is infused with a contrast agent, such as microbubbles, nanobubbles, or a phase change agent that forms microbubbles or nanobubbles when exposed to ultrasound energy. The infusion is controlled by infusion pumps 106 and 108. A dual-frequency ultrasound transducer array 110 is at least partially immersed in water tank 104. A low frequency ultrasound system 112 generates low frequency ultrasound energy and delivers the energy to a transducer array 110. Transducer array 110 transmits the low frequency ultrasound energy into simulated vessels 100 and 102 where the energy is scattered by contrast agent particles.

Transducer array 110 detects the scattered ultrasound energy at a frequency higher than the transmitted ultrasound energy and converts the scattered ultrasound signal into a radio frequency signal. A super-resolution processor 114 associated with a high frequency ultrasound system 116 detects a spatial location of a contrast agent particle in simulated vessels 100 and 102 using an algorithm to determine spatial locations of contrast agent particles based on extraction of a specific feature of the radio frequency signal. Super-resolution processor 114 generates an image of the simulated vessels by displaying a marker of the spatial location of a contrast agent particle with a resolution that is finer than the pulse length of the ultrasound pulse and repeating the detecting, converting, using, and generating for a plurality of contrast agent particles until sufficient markers have been accumulated to reconstruct a pattern of the vessel; where the pattern is an image of the at least one vessel.

Figure 2:
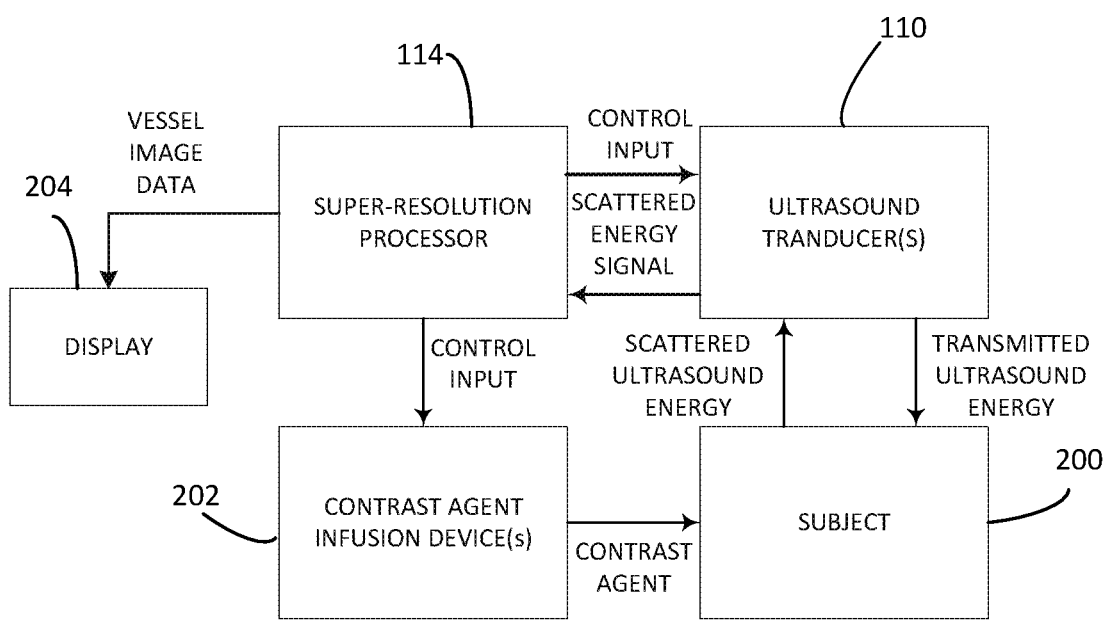
FIG. 2 is a block diagram of a system for imaging the microvasculature using dual-frequency ultrasound imaging.

FIG. 2 is a block diagram of a system for imaging a vessel using ultrasound. In FIG. 2, one or more ultrasound transducers 110 delivers ultrasound energy into at least one vessel of a subject 200, where the vessel or vessels are infused with an ultrasound enhancing contrast agent delivered by one or more contrast agent infusion devices 202. Contrast agent infusion devices 202 may be infusion pumps, syringes, or other devices capable of delivering a contrast agent into a vessel of a subject. Subject 200 may be a human, a non-human animal, or an in-vitro vessel. The vessels being imaged may be blood vessels, lymphatic vessels, or part of a venous or capillary network in a human body. In another example, endothelial cells within the vessel express a biomarker which causes the contrast agent particles to adhere to the walls of the vessel. Unlike conventional super-resolution imaging, using the system illustrated in FIG. 2, the contrast agent and the corresponding vessel structure can be imaged even when the contrast agent is not moving or moving very slowly. The contrast agent may be least one of microbubbles, nanobubbles, and are phase-change agents comprising a liquid perfluorocarbon core prior to ultrasound exposure.

The ultrasound energy delivered by ultrasound transducers 110 is scattered by the contrast agent and by structures within subject 200. However, the system illustrated in FIG. 2 can differentiate between energy scattered by the contrast agent and by other structures, in part, by transmitting an ultrasound pulse having a first frequency range and detecting scattered ultrasound energy on a second frequency range that is different from the first frequency range. In one example, the −6 dB bandwidths of the receiving and transmitting ultrasound transducers do not overlap. In another example, the −12 dB bandwidths of the receiving and transmitting ultrasound transducers do not overlap. In one example, the mean and/or the median of the second frequency range detected is at least double or at least triple the mean and/or the median of the first frequency range. In one example, ultrasound transducers 110 may deliver a single pulse of ultrasound energy to subject 200, and the scattered ultrasound energy may be first detected after transmission of the single pulse.

Ultrasound transducers 110 convert the scattered ultrasound energy into a radio frequency signal and provides the radio frequency signal to super-resolution processor 114. Super-resolution processor 114 uses an algorithm to determine a spatial location of the contrast agent particle based on extraction of a specific feature of the radio frequency signal, generates an image by displaying a marker of the spatial location of the contrast agent particle with a resolution that is finer than a pulse length of the ultrasound pulse, and repeats the processes of detecting, converting, using, and generating for a plurality of contrast agent particles until sufficient markers have been accumulated to reconstruct a pattern of the at least one vessel; wherein the pattern is an image of the at least one vessel. In one example, the resolution of the image generated by super-resolution processor 114 is at least twice as fine as the pulse length of the ultrasound pulse. For example, if the transmitted ultrasound frequency is 2 MHz, the transmitted pulse has a wavelength of 0.77 mm in soft tissue. The resolution of the resulting reconstructed image will be at least 0.335 mm. The pattern generated by super-resolution processor 114 may be an image of contrast agent particle distribution within vessels of tissue, an organ, or a tumor.

The algorithm used by super-resolution processor 114 to determine the spatial locations of contrast agent particles may include high pass filtering followed by a thresholding operation. The algorithm may utilize a centroid of the radio frequency signal produced by ultrasound transducers 110 to estimate a location of the contrast agent particle. The algorithm may include using an onset of the radio frequency signal to estimate the location of the contrast agent particle. The algorithm may also provide for computing velocity and direction of movement of the ultrasound particles. In one example, the algorithm determines the spatial location of the contrast agent particle without using a singular value decomposition filter.

Super-resolution processor 114 may output the pattern as display data to a display device 204. Display device 204 may be a display that is integrated with the ultrasound transducer or a separate display. The resulting displayed image may be similar to the image in FIG. 6A. The resolution of the displayed image may be at least twice as fine as the pulse length of the ultrasound pulse transmitted into the vessel or vessels.

Figure 3A:
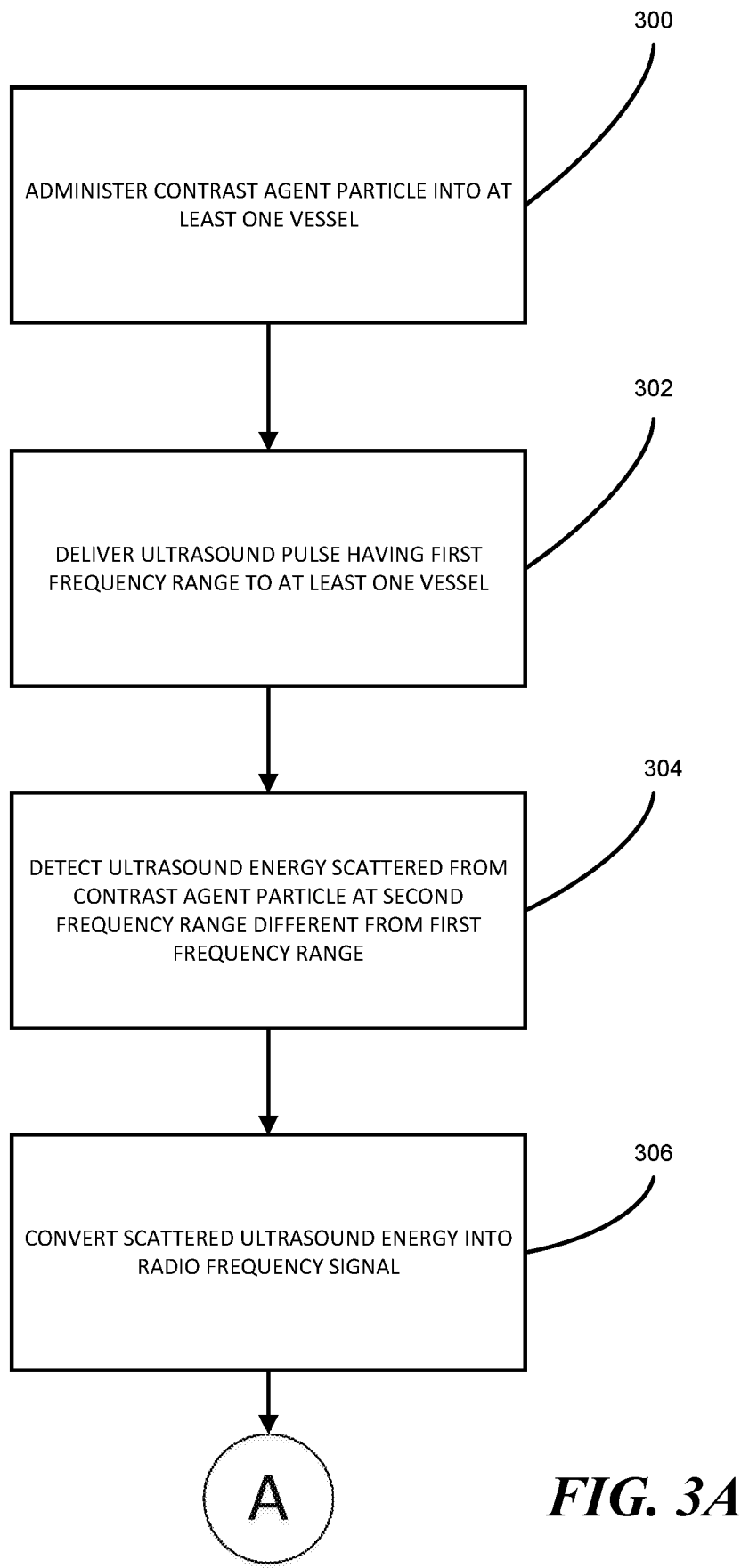
FIGS. 3A and 3B are a flow chart illustrating an exemplary process for imaging the microvasculature using dual-frequency ultrasound imaging.
Figure 3B:
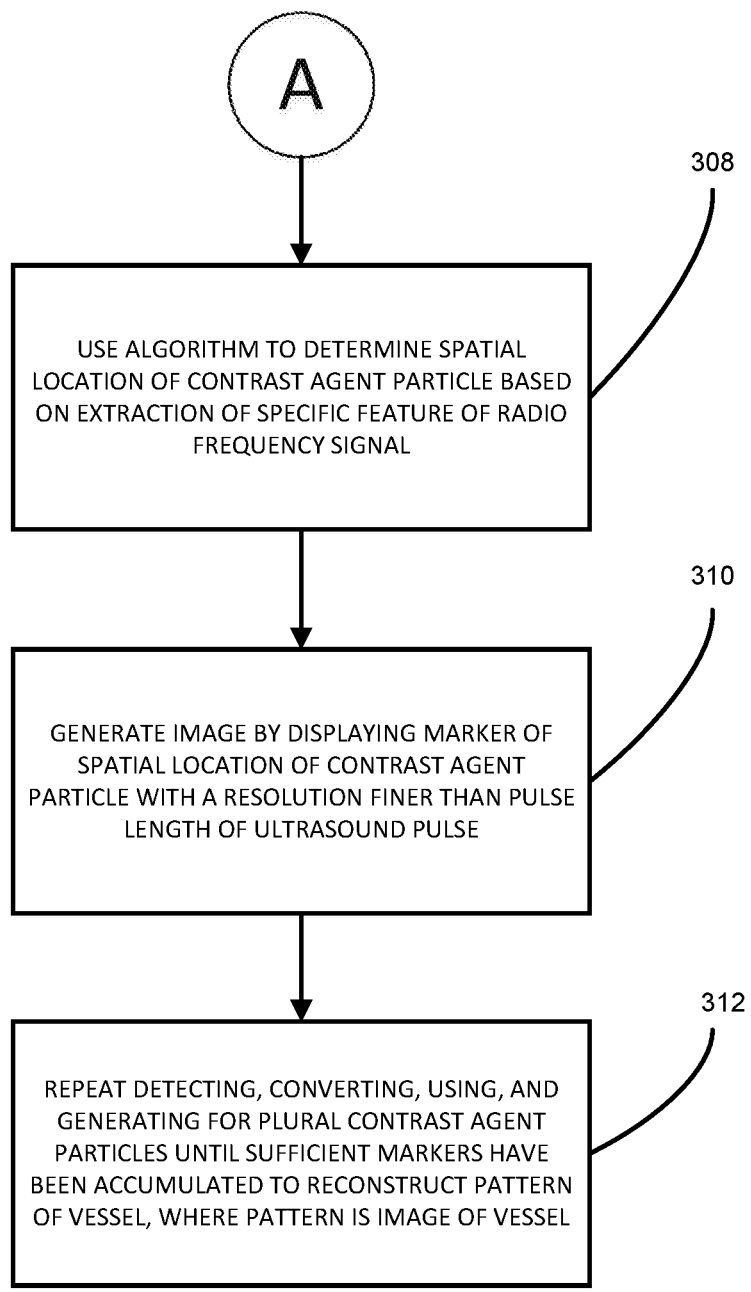

FIGS. 3A and 3B are a flow chart illustrating an exemplary process for imaging a vessel using ultrasound. Referring to FIG. 3A, in step 300, the process includes administering a contrast agent particle into the at least one vessel. For example, at least one microbubble, nanobubble, or phase change agent that comprises a perfluorocarbon having a liquid core prior to exposure to ultrasound may be infused, injected, or otherwise placed into the vessel of a subject.

In step 302, the process includes delivering an ultrasound pulse having a first frequency range to the at least one vessel. In one example, the ultrasound pulse may be a single pulse having a frequency range that is centered at 2 MHz. The first frequency range may be between 0.5 and 5 MHz. The ultrasound pulse may be transmitted simultaneously (with zero phase delay) across plural elements of the transmitting transducer to emit a plane wave into the at least one vessel.

In step 304, the process includes detecting ultrasound energy scattered from the contrast agent particle at a second frequency range that is different from the first frequency range. In one example, the second frequency range may be centered at 20 MHz. The second frequency range may be between 5 and 50 MHz. As indicated above, the first and second frequency ranges may have non-overlapping −6 dB bandwidths, −12 dB bandwidths, or both.

In step 306, the process includes converting the scattered ultrasound energy into an electronic radio frequency signal. This operation may be performed by the circuitry associated with the ultrasound transducer.

Referring to FIG. 3B, in step 308, the process includes using an algorithm to determine a spatial location of the contrast agent particle based on extraction of a specific feature of the radio frequency signal. In one example, super-resolution processor 114 may perform steps (4)-(6) above to determine the locations of contrast agent particles.

In step 310, the process includes generating an image by displaying a marker of the spatial location of the contrast agent particle with a resolution that is finer than the pulse length of the ultrasound pulse. For example, each tracked particle location may be displayed as a pixel or pixels in image data that is generated to be sent to a display device.

In step 312, the process includes repeating the detecting, converting, using, and generating for a plurality of contrast agent particles until sufficient markers have been accumulated to reconstruct a pattern of the vessel; where the pattern is an image of the vessel. For example, once a predetermined percentage of particles present in the vessel have been located, it may be determined that there is sufficient data for displaying an image of the vessel. When this occurs, the particle tracking may cease, and the final image may be displayed. The displayed image may be similar to that illustrated in FIG. 6A.

The following section illustrates a study where superharmonic imaging is used in combination with super-resolution imaging to image tubes in vitro, contrast agent flowing through the tubes, and rodent vessels in vivo.

Superharmonic Ultrasound for Motion-Independent Localization Microscopy: Applications to Microvascular Imaging From Low to High Flow Rates Recent advances in high frame rate biomedical ultrasound have led to the development of ultrasound localization microscopy (ULM), a method of imaging microbubble (MB) contrast agents beyond the diffraction limit of conventional coherent imaging techniques. By localizing and tracking the positions of thousands of individual MBs, ultrahigh resolution vascular maps are generated which can be further analyzed to study disease. Isolating bubble echoes from tissue signal is a key requirement for super-resolution imaging which relies on the spatiotemporal separability and localization of the bubble signals. To date, this has been accomplished either during acquisition using contrast imaging sequences or post-beamforming by applying a spatiotemporal filter to the b-mode images. Superharmonic imaging (SHI) is another contrast imaging method that separates bubbles from tissue based on their strongly nonlinear acoustic properties. This approach is highly sensitive, and, unlike spatiotemporal filters, it does not require decorrelation of contrast agent signals. Since this superharmonic method does not rely on bubble velocity, it can detect completely stationary and moving bubbles alike. In this work, we apply SHI to ULM and demonstrate an average improvement in SNR of 10.3-dB in vitro when compared with the standard singular value decomposition filter approach and an increase in SNR at low flow (0.27 µm/frame) from 5 to 16.5 dB. Additionally, we apply this method to imaging a rodent kidney in vivo and measure vessels as small as 20 µm in diameter after motion correction.

I. INTRODUCTION

Recently, super-resolution imaging with ultrasound localization microscopy (ULM) has attracted attention because it resolves blood vessels on the order of a few microns in diameter at centimeters in depth in vivo [1], [2]. A model relating the spatial localization error of microbubble (MB) contrast agents to arrival time estimation error predicts that for certain in vivo scenarios, such as human breast imaging, ULM will achieve resolutions on the order of 1 µm [3]. It has long been known that abnormal angiogenesis and vascular morphology are biomarkers for different diseases, including diabetes, inflammatory conditions, and cancer [4], [5]. Recently, imaging abnormal angiogenesis with ultrasound microvascular imaging techniques has been proposed as a method of identifying malignancies [6]-[8]. In this context, ULM has shown diagnostic potential by measuring tortuosity of blood vessel structure in subcutaneous tumors in a rodent model [9]. In addition to providing morphological data, ULM is also able to provide accurate quantification of blood flow velocity, which can be combined with other metrics, such as vessel distances, to create a rich characterization of the imaging target [10].

Many different approaches to ULM are present in the literature, although the method for generating a super-resolved image with ultrasound can be described by three general components [11]. First, MB contrast agents are administered intravenously, and a series of frames is acquired (normally hundreds to hundreds of thousands). While some groups have reported success with clinical scanners constrained to lower frame rates (<100 Hz) [2], [10], generally a high frame rate on the order of 1-10 kHz is used to perform accurate velocimetry after target localization. Second, the data set is processed to separate MB and tissue signals, which overlap in conventional ultrasound imaging. Popular approaches to this step will be subsequently discussed in this section. Finally, MBs are localized in each frame with subwavelength accuracy, and the positions are accumulated on a high-resolution grid. The bubble positions are typically tracked between frames to also create high-resolution blood velocity maps [2].

As mentioned previously, a crucial step to the process of generating a ULM image is the separation of MB signals from background tissue signal. The most popular method of suppressing tissue speckle prior to localization is a filter based on singular value decomposition (SVD). The SVD filter isolates MBs by taking advantage of the different spatiotemporal coherences of tissue speckle and contrast agents [12], [13]. Although the MBs and tissue may be moving with the same velocity magnitude, the fact that the MBs are localized in space implies that they have far smaller spatial coherence lengths in the beamformed images. When tissue is relatively static within an ultrafast ensemble, its features tend to be represented in the first singular vectors, where the right singular vectors (also called temporal singular vectors in this context) have most of their energy near 0 Hz [12], [14]. Blood, on the other hand, flows at a range of velocities, and its scatterers decorrelate at varying rates over the course of an acquisition. Crucially, these scatterers decorrelate in spatially localized regions of the image. The energy from these scatterers, thus, tends to occupy a subspace of higher singular vectors in which the spatiotemporal vectors are higher frequency than those corresponding to tissue. As long as there is sufficient separation between the vector subspaces occupied by tissue and blood flow, a data set can be filtered to remove the tissue.

However, in the slow-flow regime, the tissue and blood singular vector subspaces significantly overlap, especially since the bubble signal can be orders of magnitude smaller than the tissue signal. Due to this low contrast, they can be
    impossible to tease apart. In [13], it was demonstrated that SVD filtering of an ultrafast ensemble of b-mode images using a commercially available contrast agent in a flow phantom resulted in contrast-to-tissue ratios (CTRs) of 11 and 25 dB for flow rates of 2 and 20 mm/s, respectively, when imaging at 3000 frames/s. Furthermore, [14] has documented the difficulty in determining an appropriate singular vector threshold for the SVD filter in vivo. In their study, the most successful of 13 different threshold estimators was able to achieve a CTR within 10% of the maximum CTR for only 74% of in vivo data sets. The results are even worse for their manual threshold selection, where a relative CTR difference of 10% or less was achieved for only 13% of data sets. Although SVD-based processing has produced many impressive ULM images ([1], [9]), the results of [14] suggest that the performance of such a filter may suffer when applied to the smallest of capillaries where peak blood velocity ranges between 0.2 and 1.7 mm/s [15], [16]. Furthermore, SVD may not be appropriate for new applications, such as super resolution molecular imaging, in which bubbles would exhibit no motion relative to the tissue.

Another approach to contrast enhancement that has been used for ULM is nonlinear imaging [2], [17]. While spatiotemporal processing methods rely on the motion of contrast agents relative to tissue in slow time, nonlinear imaging sequences rely on the fact that MB contrast agents generate significantly more harmonic energy than tissue under most circumstances. For example, one study reports that imaging at 1.7-MHz center frequency results in a second harmonic that is 24-dB down compared with the fundamental for tissue and around 9-dB down for MBs [18]. To date, methods such as pulse inversion [19], amplitude modulation [20], [21], and more sophisticated combinations of phase and amplitude modulation [22] have achieved CTR on the order of 50 dB with commercially available contrast agents.

Superharmonic imaging (SHI) is a method of contrast-enhanced ultrasound that reconstructs images using the third- and higher order harmonics of the fundamental frequency of the transmit waveform [18]. The advantage of SHI is an improvement in CTR compared with fundamental and second harmonic imaging (40-dB increase reported in [18]), along with an increased resolution from the higher frequencies and reduced sidelobes [23]. These improvements come at the cost of decreased imaging performance at depth because of the rapid attenuation of high-frequency (HF) waves in tissue. SHI is extensively used for vascular imaging with an approach called acoustic angiography (AA) [24]. In the
    previously mentioned study, an AA image is generated by receiving from the third to approximately the tenth harmonic of the MB frequency response by using an ultrawideband dual-frequency (DF) transducer (transmit center frequency: 4 MHz, receive center frequency: 30 MHz, both roughly 100% relative bandwidth), producing images of blood vessels with a resolution of approximately 150 μm. It has been shown that AA is able to resolve microvasculature in vivo with high CTR in both rodents and humans [24], [25], although this technique remains fundamentally diffraction limited.

Thus, in this document, we report a combination of SHI and super-resolution processing without the SVD filter. In this manner, we eliminate the need to detect MBs through their spatiotemporal coherence, and we also overcome the diffraction limitation of SHI. In this article, superharmonic ULM is performed using a novel DF array system with transmission at 1.7 MHz and a receive bandwidth centered at 20 MHz [26]. In vitro, we image a 46-μm inner diameter tube and compare the sensitivities of SHI- and SVD-based approaches to ULM with respect to flow velocity. In vivo, we target the rodent kidney and discuss strategies for motion correction in a DF imaging scheme. For both in vitro and in vivo studies, we compare the resolution of the images to AA maximum intensity projections (MIPs). Finally, we discuss the strengths and weaknesses of SHI for ULM along with areas of future work.

II. MATERIALS AND METHODS

A. Experimental Setup

1) Contrast Agent Preparation: MBs were prepared in-house according to [27]. Briefly, a 1-mM lipid solution comprising 90 mole % 1, 2-distearoyl-sn-glycero-3-phosphocholine and 10 mole % 1, 2-dipalmitoyl-sn-glycero-3-phosphoethanolamine-N-[methoxy(polyethylene glycol)-2000] was formulated in phosphate-buffered saline containing 15% (v/v) propylene glycol and 5% (v/v) glycerol. Aseptic lipid solution was packaged into 3-mL glass vials, and the air headspace was exchanged with decafluorobutane ($C_4F_{10}$) prior to creating the MB emulsion by shaking in a VialMix (Lantheus Medical Imaging, N. Billerica, MA). Concentration and size distribution of the MB contrast agent were measured using an Accusizer 780 AD (Entegris, Billerica, MA); typical concentration was 3E10 MB/mL with an average diameter of 0.97 µm±0.51 µm (mode=0.6 µm, median=0.9 µm).

Figure 4A:
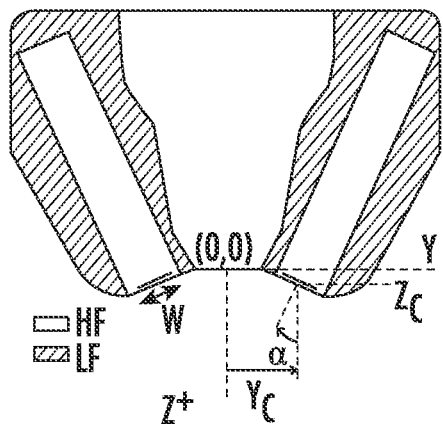
FIG. 4A is a schematic diagram of the elevation cross section of the dual frequency (DF) assembly with low frequency (LF) transducers (outer two transducers) and high frequency (HF) array (center transducer). W=2.9 mm, α=27°, $(y_c, z_c)$=(8.45 mm, 0.73 mm)
Figure 4B:
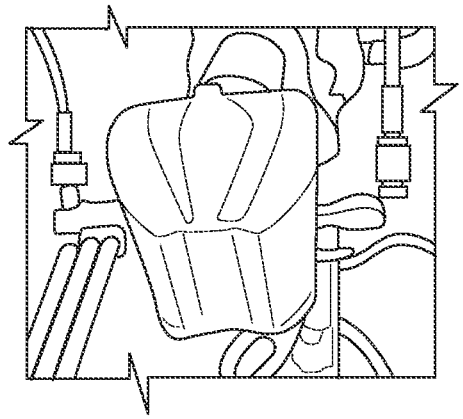
FIG. 4B is an image of the DF probe used in experiments, illustrating the 1.7 MHz LF transducers running parallel to the 21-MHz HF transducer array on the front face.
Figure 4C:
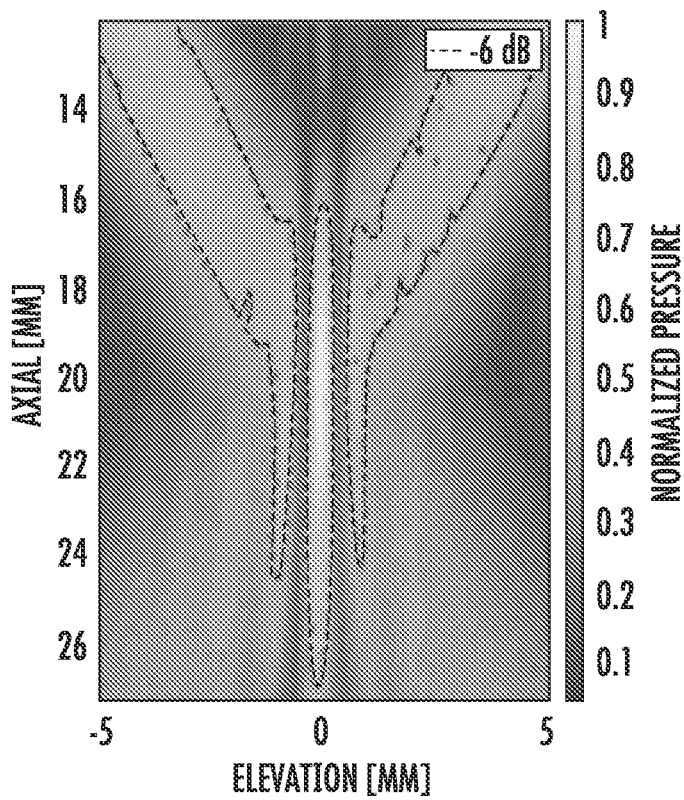
FIG. 4C is Hydrophone measurement of the LF beam pattern in the elevational-axial plane. The −6-dB contour of the beam is marked with a dashed line. The axial dimension is measured relative to the face of the HF array.

2) DF Transducer: A custom DF probe described in [26] was used for all imaging in this study (see FIG. 4A). Briefly, it consists of a commercial 256-element linear array transducer (MS250, VisualSonics, Toronto, Canada) outfitted with two low-frequency (LF) elements. The LF transmit beam has a depth of field of 11 mm with peak pressure at 20 mm in the axial dimension. The HF array has a center frequency measured at 18 MHz and relative bandwidth of 70%, while the LF elements have a center frequency of 1.7 MHz and relative bandwidth of 78%. This transducer can be operated in DF mode by transmitting with the LF elements and receiving with the HF array and in conventional mode by transmitting and receiving with the HF array. When operating in the DF mode, the transmit pulse is a single-cycle, cosine-windowed sine wave with a center frequency of 1.7 MHz [28]. The LF elements are driven by an arbitrary waveform generator (AWG 2021, Tektronix, Beaverton, OR, USA) connected to a 50-dB radio frequency (RF) power amplifier (240 L, ENI, Rochester, NY, USA). Receiving with the HF array is controlled by a Vantage 256 scanner (HF configuration, Verasonics, Kirkland, WA).

B. ULM Imaging Scheme

All ULM images illustrated in the accompanying figures were generated using the DF mode with a pulse repetition frequency (PRF) of 500 Hz at a mechanical index (MI) of 0.24 for a total of 25000 frames. RF data were beamformed offline on a 10-µm grid and thresholded to remove background noise (threshold empirically determined). Bubbles were localized using peak detection with an isotropic Gaussian aperture with an RMS width of 100 µm and tracked between frames using a nearest neighbors approach with a maximum linking distance of 100 µm between frames. For comparison, a superharmonic MIP was generated from the stack of DF images used to create the ULM image.

C. Tube Imaging In Vitro

A resolution phantom was made using two microtubes made of fluorinated ethylene propylene, each with an inner diameter of 46 µm (measured optically with a calibrated microscope). The phantom was submerged in a water bath, and the tubes crossed in an "X" configuration at a depth of approximately 20 mm. A dilution of MBs in saline with a concentration of 1E7 MB/mL was prepared and infused through both tubes in opposite directions at 10 µL/min using an infusion pump (Harvard Apparatus, Holliston, MA). The tubes were imaged according to the protocol described in Section II-B, and the average tube profiles were measured within the same ROI for ULM and AA images for comparison.

D. Flow Study In Vitro

A cellulose tube with an inner diameter of 200 µm was suspended in a water bath at a depth of 20 mm. A dilution of MB in saline with concentration 1E7 MB/mL was infused through the tube at volume flow rates ranging between 0.25 and 15.0 µL/min using an infusion pump (Harvard Apparatus, Holliston, MA). These flow rates correspond to the mean displacements of 0.27 and 15.90 µm/frame. Before collecting data for each trial, the tube was flushed with air and water and reinfused with a newly prepared dilution of contrast agent. Infusion was allowed to proceed for a minimum of 3 min before imaging to ensure that the velocity of the contrast agent in the tube had reached steady state. For each trial, 1000 frames were acquired, and three trials for each modality per flow rate were performed. DF frames were collected according to Section II-B, while b-mode frames were collected at an MI of 0.11 (center frequency=15.6 MHz) and a PRF of 500 Hz.

Each batch of b-mode images was SVD filtered as follows:

1) arranged the beamformed RF data into the Casorati matrix in which columns are vectorized b-mode frames; 2) performed an SVD on this matrix; 3) zeroed all singular values for the first 15 singular vectors (empirically determined); and 4) reconstructed the b-mode frames with the new set of singular values. Each set of 1000 frames was then used to generate an MIP, which was normalized and converted to decibels. A reference b-mode frame was used to draw a pair of ROIs corresponding to the tube and the background. SNR in this experiment is defined as the difference between the maximum value of the tube ROI and the average magnitude within the background ROI. This definition has been chosen to account for the sparse number of bubbles present in each MIP for the slower flow rates because averaging within a tube ROI artificially lowers the SNR for each trial by including gaps between bubbles in the average calculation.

E. Kidney Imaging In Vivo

Figure 5A:
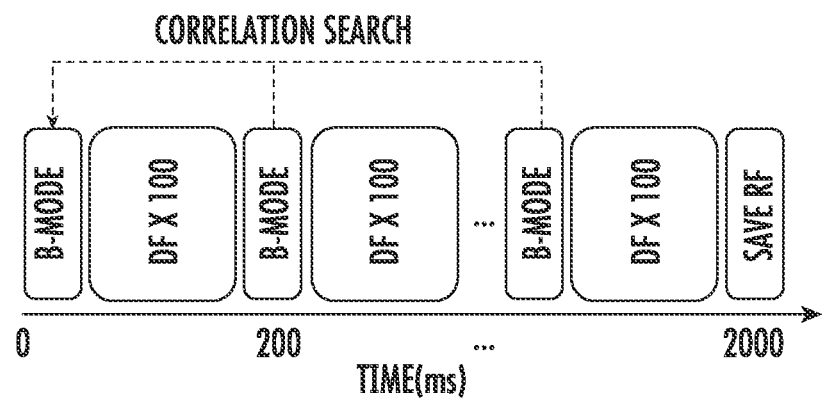
FIGS. 5A-5C illustrate an overview of data collection and processing for superharmonic ULM.
Figure 5B:
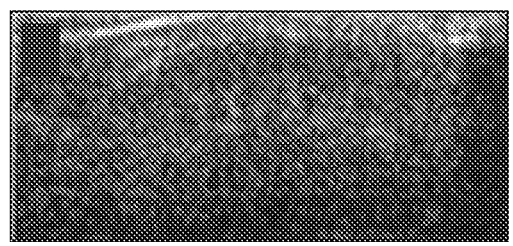

In vivo imaging was performed in healthy female Fischer 344 rats (Charles River Laboratories, Durham, NC) according to a protocol approved by the Institutional Animal Care and Use committee at the University of North Carolina at Chapel Hill. A polydisperse population of MB contrast agent (mean=0.97 µm, standard deviation=0.51 µm) was diluted to 1E9 MB/mL and administered via a catheter placed in the tail vein at 25 µL/min using a syringe pump (Harvard Apparatus, Holliston, MA). Infusion was allowed to proceed for 3 min prior to any imaging to allow the concentration of contrast in circulation to approach steady state. DF images were collected and processed according to the parameters in Section II-B. To estimate physiological motion, b-mode frames were interleaved between every 100 DF acquisitions [see FIG. 5A]. 2-D speckle tracking was performed on adjacent b-mode frames according to [29] with a square 2-mm kernel (approximately 20 HF wavelengths in either dimension), ±150-µm search window with 1-pixel step size, and 50-µm steps between adjacent kernels [see FIG. 5B]. The displacement grid for each time step was spatially interpolated to match the 10-µm pixel size of the original image.

Figure 5C:
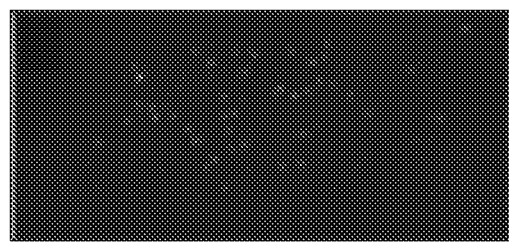

To estimate the tissue displacement for a given DF image [see FIG. 5C], linear interpolation is performed through the slow time dimension between consecutive displacement arrays. Then, for each DF image, detected bubble locations are adjusted based on the estimated deformation of the tissue at that time point. Bubble localizations are also weighted in the final image according to the peak correlation coefficient associated with the bubble's parent patch during motion estimation. For example, if the correlation search is able to find a perfect match, the bubble's localization is given a value of 1, whereas a poor match might result in the bubble being weighted at 0.5. Bubbles below a correlation threshold of 0.3 are completely filtered from the analysis. The accuracy of the speckle tracking depends partially on how much the target decorrelates as a result of motion [30]. Therefore, contributions to the final ULM image were weighted by the correlation coefficient from the speckle tracking in order to minimize the effect of inaccurate displacement estimation on image quality. The correlation threshold of 0.3 for completely removing a localization was empirically determined. Between frames, MB centroids are linked using the nearest neighbor approach, and these line segments are drawn to create the final image. The diameters of selected vessels in ULM images were determined by taking the average of multiple full-width at half-maximum (FWHM) measurements along the axis of each vessel.

Three-dimensional imaging was accomplished by using a linear motion stage (XSlide, Velmex, Inc., NY, USA) controlled by a custom LabVIEW program (National Instruments, TX, USA) to mechanically sweep the ultrasound transducer in the elevational dimension. A total of 25 000 DF frames were acquired at each position, and each position was spaced by 500 μm.

III. RESULTS

A. Tube Imaging In Vitro

Figure 6A:
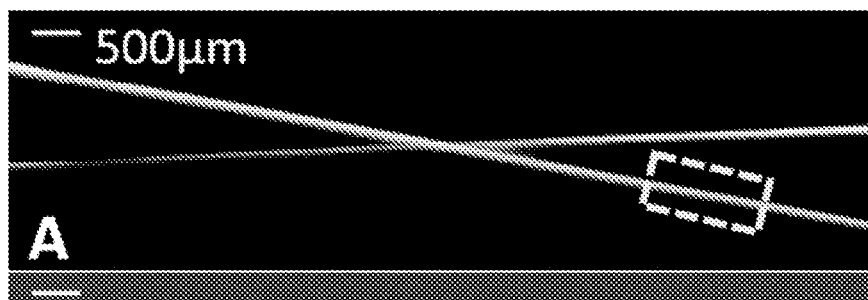
FIGS. 6A-6C illustrate a comparison of super harmonic imaging—ultrasound localization microscopy (SHI-ULM) and acoustic angiography (AA), which is a superharmonic imaging technique, using a pair of 46-μm tubes in a water bath. The scale bars in the upper left-hand corners of FIGS. 6A and 6B are 500 μm.
Figure 6B:
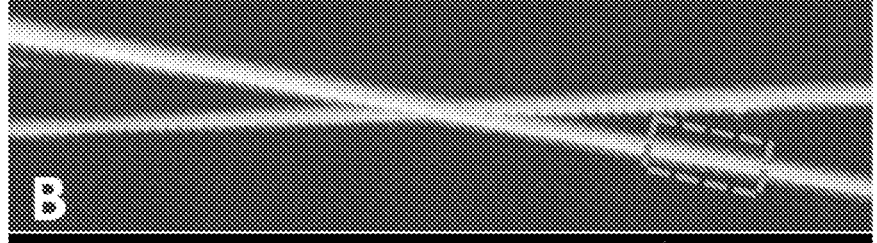
Figure 6C:
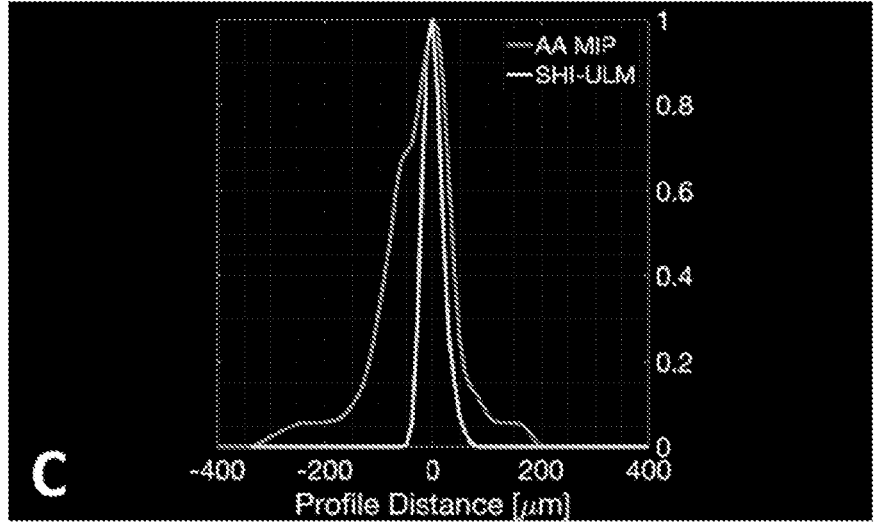
Figure 7A:
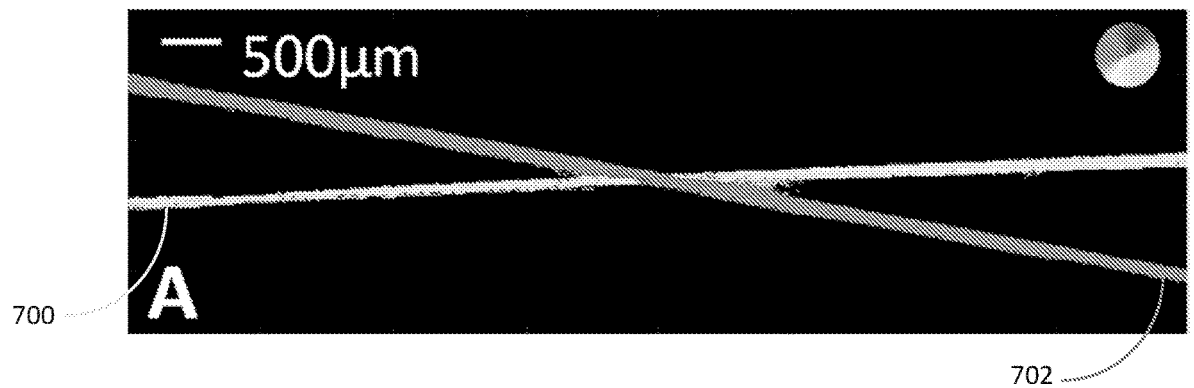
FIGS. 7A and 7B are velocity maps of crossed 46-μm tubes in a water bath. The scale bars in the top left hand corners of FIGS. 7A and 7B are 500 μm.
Figure 7B:
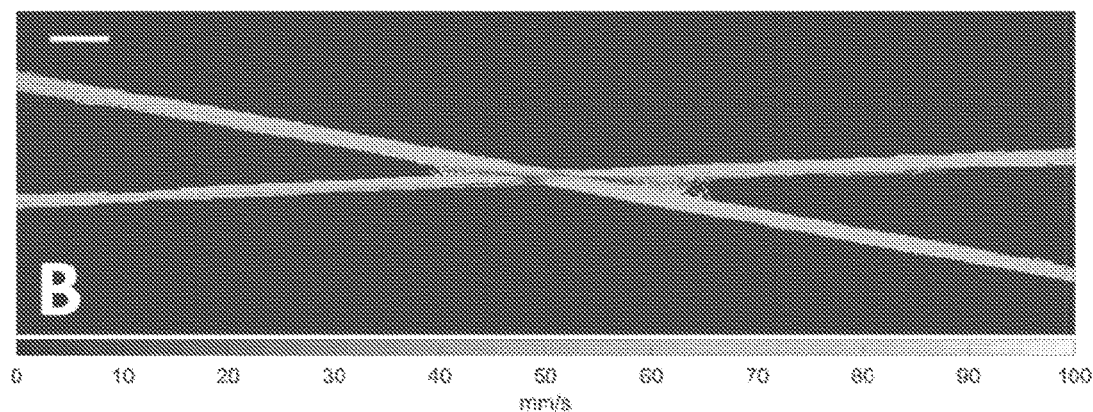

A ULM image was generated with 25000 frames using a 1.7-MHz plane wave transmission and a receive center frequency of 15.6 MHz [see FIG. 6A]. The average FWHM values measured within the regions of interest shown in FIGS. 6A and 6B were 44 μm for the ULM image and 113 μm for the superharmonic MIP [see FIG. 6B]. These average profiles are overlaid for comparison in FIG. 6C. Maps of velocity direction [see FIG. 7A] and magnitude [see FIG. 7B] were also created. From FIG. 7A, the mean angles of flow for these tubes were measured to be 3.0° and 169.3°, which correspond with the tubes 700 and 702, respectively. From FIG. 7B, the average velocity magnitude within the tubes was measured to be 67.5 mm/s. For a 46-μm tube, a volume flow rate of 10 μL/min corresponds to an average velocity of 100.3 mm/s through a cross section of the tube. Applying a ⅔ correction factor to account for integrating through elevation [31] predicts the average velocity measured in the ULM imaging plane to be 66.9 mm/s, which agrees well with the measurement;

B. Flow Study In Vitro

MIPs for all the flow rates and trials were created, and examples of slow- and fast-flow MIPs are provided in FIGS. 8A-8D. The MIPs were generated by envelope detecting the beamformed RF data and taking the maximum through time for each pixel.

Figure 9:
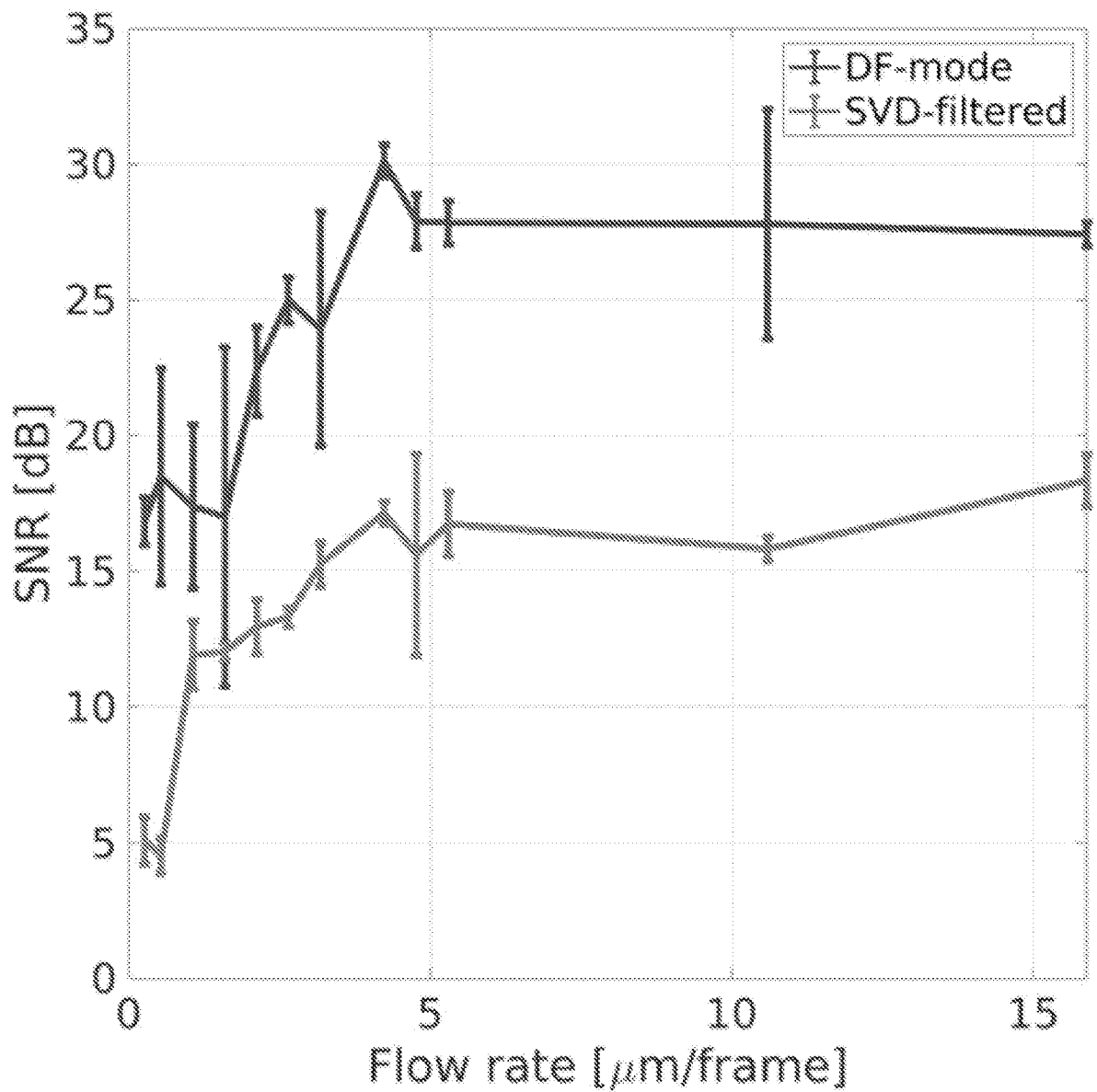
FIG. 9 is a graph of SNR versus flow rate for DF and SVD-filtered images. The upper plot in FIG. 9 is for DF-filtered images, and the lower plot in FIG. 9 is for SVD-filtered images. DF imaging results in an average improvement of 10.3 dB over SVD imaging, even at slow flow rates below 5 microns/frame.

When infusing a 200-μm tube at 0.25 μL/min and imaging at 500 frames/s, SHI produces an average SNR of 16.5 dB over three trials [see FIG. 8A]. Increasing the volume flow rate to 15 μL/min and holding frame rate constant increases the SNR to 27.4 dB [see FIG. 8B]. SVD filtering produces SNR values of 5.1 dB [see FIG. 8C] and 18.3 dB [see FIG. 8D] for the slow- and fast-flow conditions, respectively. Across all flow rates, SHI produces an average improvement in SNR of 10.3 dB compared with SVD filtering (see FIG. 9).

C. Kidney Imaging In Vivo

Figures 10A, 10B, 10C:
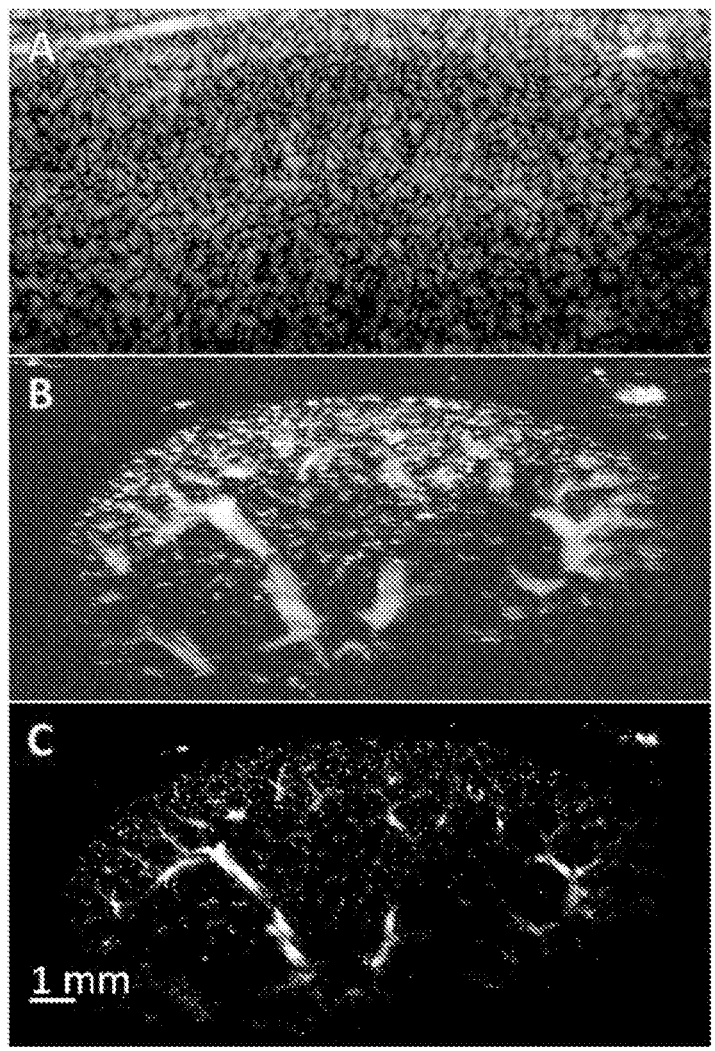
FIGS. 10A-10C illustrate examples of SHI-ULM applied to a rodent kidney with motion correction.
Figures 11A, 11B, 11C, 11D:
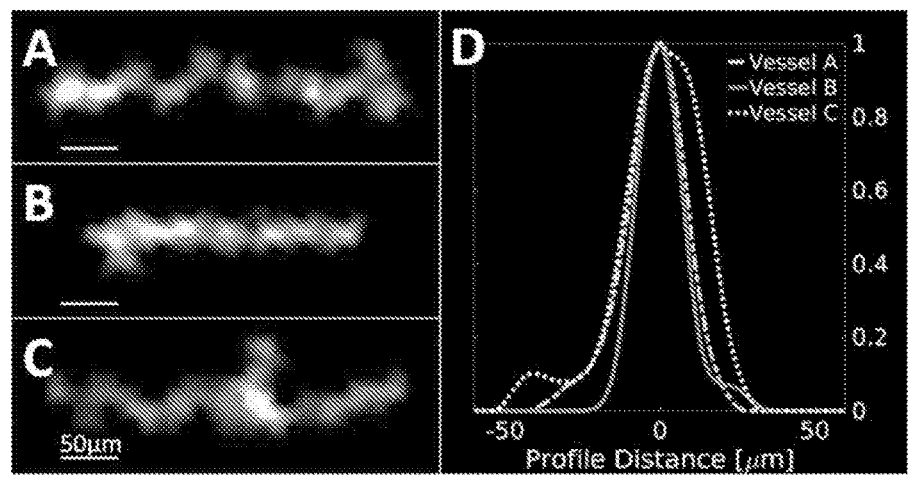
FIGS. 11A-11C illustrate selected vessels from the rodent kidney 3-D data set. More particularly.
FIG. 11D is a graph illustrating average profiles of the vessels in FIGS. 11A-11C with FWHM values of 20.9, 17.2, and 29.1 μm, respectively.
Figures 13A, 13B:
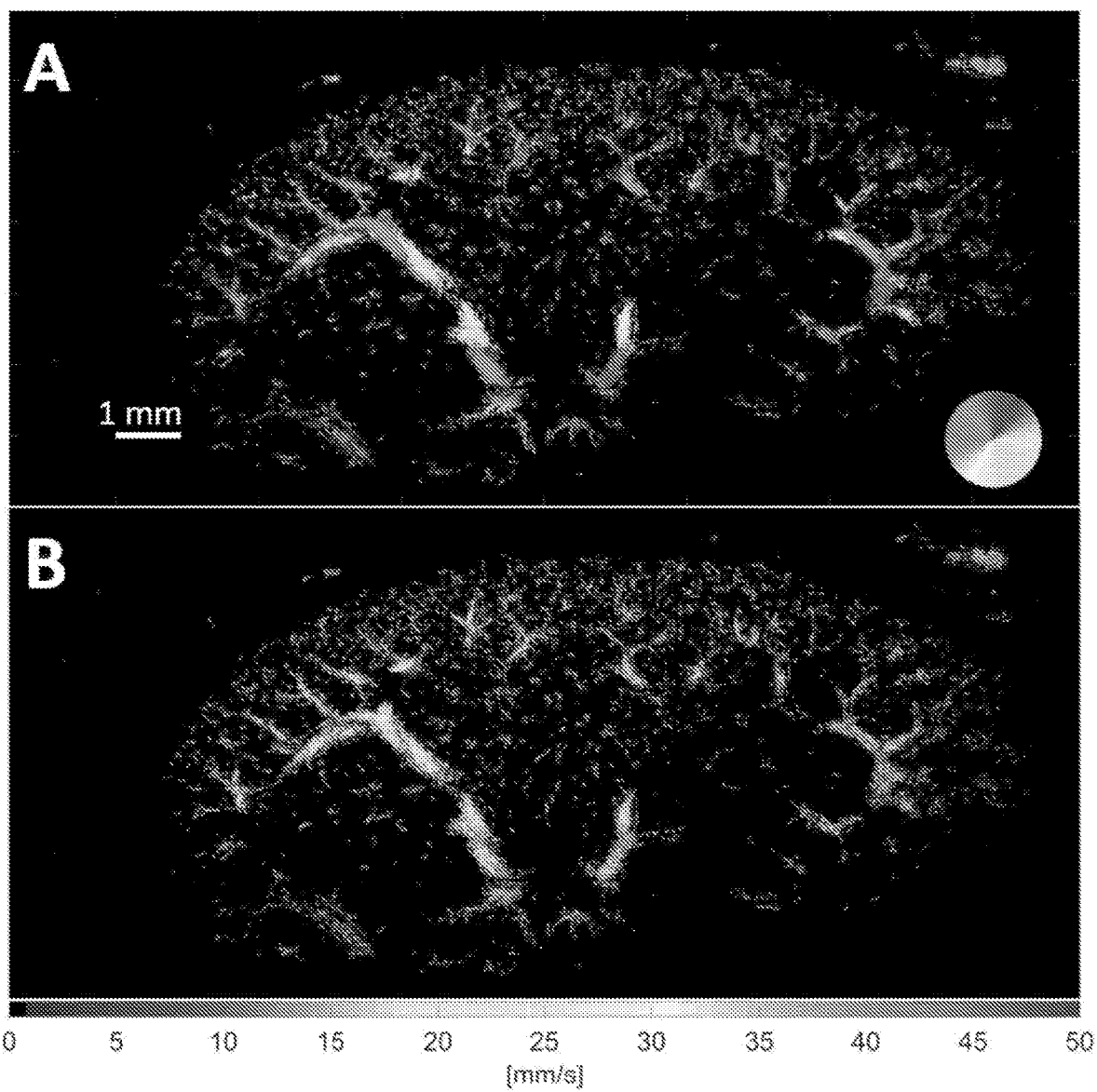
FIGS. 13A and 13B are velocity maps tracking bubbles in vivo allows for the mapping of blood velocity in a rodent kidney.
Figure 14:
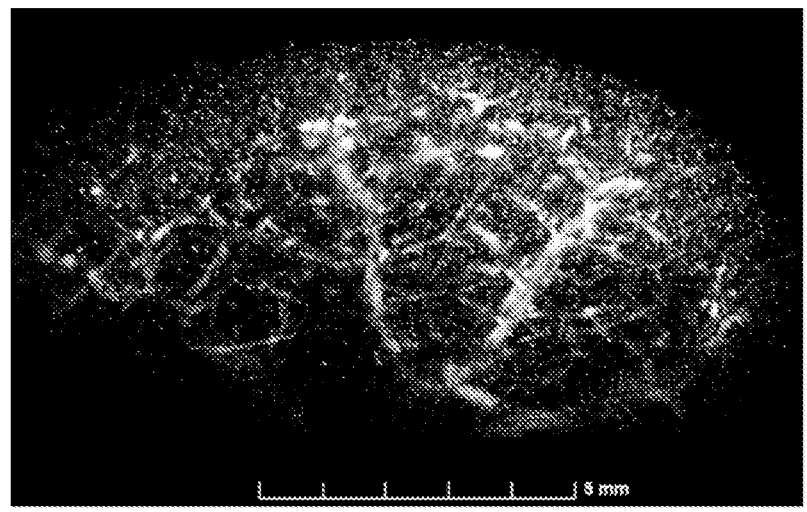
FIG. 14 is an example of a 3-D SHI-ULM by mechanically scanning the transducer in the elevational dimension. This image was generated with 17 slices spaced at 500 μm and contains vessels on the order of 20 μm.

A superharmonic ULM image of a rodent kidney was generated from 25000 DF frames (500-Hz PRF and MI of 0.24) and shows the ability to resolve vessels on the order of 20 μm in diameter (see FIGS. 10A-10C). For comparison, a conventional b-mode frame [see FIG. 10A] and a superharmonic MIP [(see FIG. 10B)] are provided. Selected vessels from this ULM data set have average FWHM values of 20.9, 17.2, and 29.1 μm [see FIGS. 11A-11C]. The average profiles are provided for comparison in FIG. 11D. A ULM image was created from the same data set without applying motion correction to demonstrate the effects of large magnitude respiratory and cardiac artifacts on image quality [see FIG. 12A]. A qualitative visualization of the performance of the motion correction based on sparsely interleaved b-mode frames and speckle tracking is provided in FIG. 12B. FIGS. 13A and 13B contain the velocity maps corresponding to the motion-corrected ULM frame shown in FIG. 10C. By mechanically scanning the imaging probe in the elevational dimension, three-dimensional ULM data sets were acquired. FIG. 14 shows an MIP for a rodent kidney data set (rendered using 3-D Slicer 4.10.2, Kitware, Clifton Park, NY). This volume was generated from 17 slices spaced by 500 μm with 25000 DF frames per slice.

IV. DISCUSSION

A new approach to ULM using SHI has been demonstrated both in vitro and in vivo, resolving vessels on the order of 20 μm in diameter in a rodent kidney. SHI offers greater CTR than traditional contrast pulse sequences or SVD filtering while still allowing for motion correction by sparsely interleaving HF b-mode frames into the imaging sequence (1-100 ratio). With a DF arrangement, it is also possible to image slowly moving contrast agents in a cellulose tube in a water bath with much higher SNR than an SVD-based approach. This improvement in SNR may decrease the variance in spatial localizations of slow MB contrast agents, which has been modeled as a linear function of the Cramer-Rao lower bound (CRLB) for time delay estimates [3], [30]. The CRLB itself increases strongly as SNR decreases below 10 dB, holding other parameters constant. For applications such as molecular imaging, for which the aim is to image stationary bubbles, ULM with SVD filtering may prove challenging even in the absence of physiological motion, assuming that MB contrast agents do not decorrelate through slow time.

Interestingly, the results of this flow study revealed a dependence of SNR on flow rate in SHI. It is possible that this phenomenon is related to the polydispersity of the contrast agent dilution. The majority of the MBs used in this study are around 1 μm in diameter, which have resonance frequencies higher than the 1.7-MHz transmit pulse [32], [33]. For higher flow rates, there is an increased probability that a large bubble with a resonant frequency closer to the LF element center frequency will pass through the field of view during the 1000-frame acquisition. For slower flow rates, bubbles do not traverse the full length of the tube during a 1000-frame acquisition [see FIG. 8A]. This means that if a large bubble is not present at the onset of data collection, it is unlikely that one will appear in the tube before all the frames for that particular trial have been collected. A monodisperse population of bubbles may flatten the SNR versus flow rate curve for SHI, though this was not investigated.

The study of SNR versus flow rate suffers from some drawbacks, however, such as the relatively low number of trials for each set of parameters (n=3), which may affect the results shown in FIGS. 8A-8D and 9. Even with its limitations, the results of this study suggest that DF imaging outperforms SVD filtering in terms of SNR for all the flow rates tested between 0.27 and 15.90 μm/frame and that SHI is better suited for imaging slowly moving contrast agents in a tube when imaging at 500 frames/s. It is important to consider that the performance of the SVD filter depends on both particle speed and frame rate; hence, we report the results as SNR versus microns per frame.

In vitro images of a 46-µm tube resulted in an average FWHM measurement of 44 µm, an error of 4.3%. In vivo, it is quite difficult to assess the accuracy of the ULM imaging without ground truth information regarding the diameter of individual vessels. However, we believe that given the theoretical resolution limit of this system derived in [3] along with the measured error reported earlier, we are justified in assuming the diameters of the selected vessels shown in FIGS. 11A-11C to be on the order of 20-30 µm, if not smaller. If we assume the resolution error of this system is a fixed 2-µm bias rather than 4.3% of the real value, then the vessels shown in 11A-11C would measure 22.9, 19.2, and 31.1 µm. In any case, these measurements are well below the diffraction-limited resolution of the HF array and were collected in a freely breathing rodent without physical constraints.

One limitation of SHI-ULM is the shallow depth of penetration based on the high center frequency of the receiving transducer. This configuration is well suited for many preclinical scenarios and superficial clinical targets and less so for larger animals and the majority of human organs. However, prior clinical studies have demonstrated SHI of microvasculature in the human breast at 25 MHz at less than 2 cm, and we have demonstrated the ability to image microvasculature as deep as 4 cm at 20 MHz in a rodent cancer model [34].

Thus, we hypothesize that SHI-ULM will be relevant for transcutaneous assessment of abnormal angiogenesis or other vascular pathologies in the breast, prostate, thyroid, or other shallow organs and could be used for deeper organs endoscopically.

Although this study was limited to small animal imaging and in vitro experiments, the probe used in this work shows an improvement over previous state of the art devices in SHI in terms of imaging depth, depth of field, and frame rate. For translation to a clinical population, further study is needed regarding optimal transducer design parameters for an appropriate balance between CTR and imaging depth for DF ultrasonic imaging.

Another limitation unique to SHI for ULM is the MI (>0.2) necessary to achieve adequate CTR. In these studies, we utilized MIs up to 0.24. While we expect these parameters to be safe based on [35]-[37], this MI is partially destructive to bubbles over repeated pulsing. This might be especially problematic for imaging small capillaries, in which MBs may require time scales on the order of minutes to traverse the entire path length of an individual capillary [38]. For this reason, it may provide additional benefit in the future to explore optimization of experimental parameters including frame rate, MI, MB formulation and stability, MB concentration, infusion rate, and others in an effort to realize the full potential of the SHI approach for ULM.

Another challenge associated with this imaging method is the unique point spread function produced by SHI. Under the right circumstances, a single contrast agent will exhibit a point spread function which is multimodal in the axial dimension due to the strongly nonlinear vibrations of the bubble shell. The presence of such an artifact has a negative impact on the final image quality if not accounted for because current popular localization methods were not designed with such a phenomenon in mind [39]. In order to control this issue, we have tuned the transmit pressure to attain sufficient CTR for accurate localization while minimizing the multimodal artifact. This approach, combined with noise thresholding, proved sufficient to mitigate the deleterious effects of the superharmonic artifact. Another approach that can be explored in the future is designing a localization process tailored to the presence of this artifact such that higher MI pulses can be employed to further improve CTR.

It should be noted that the results of this study are strongly independent on the characteristics of the contrast agent used during imaging. Recent work has examined the relationship between MB parameters and their influence on superharmonic response [40]. One critical parameter is the resonance frequency of the contrast agent, which is largely determined by its diameter [33]. Driving bubbles at or near their resonance frequency leads to strongly nonlinear oscillations of the shell and hence contributes to generating higher harmonics. The results of [40] demonstrate that the in-house bubbles used for this study are comparable to commercially available contrast agents, such as Definity and Micromarker, in terms of superharmonic backscatter. This finding suggests that the imaging methods described in this work can be replicated in clinical or preclinical settings using commercial bubbles.

One subject that is not studied in this work is the effect of the transducer geometry on ULM image quality. It is certain that the "X" configuration of the LF elements results in appreciable transmit pressures away from the HF array's imaging plane [see FIG. 1(c)]. While off-target bubbles are sonicated on transmit, hydrophone measurements show the elevational beamwidth of the HF transducer ranges between 0.5 and 1.0 mm over the main lobe of the LF transmission. It follows that this system is not sensitive to contrast agents that are more than 0.5 mm out of plane. However, we must consider the depth-dependent response of the system imposed by the broadening HF beamwidth. Precisely controlling the contrast concentration in the blood pool ensures that we retain a sparse group of bubbles in each frame even as we receive with a thicker beam at greater depths. Another source of depth dependence that is not directly accounted for in this study is the variable amplitude of the transmitted pressure in the axial dimension which is given by the degree of overlap between the crossed LF beams. It should be noted, however, that these specific limitations are unique to this sort of transducer design and are not necessarily associated with DF imaging in general.

As mentioned previously, the current system is suitable for imaging preclinical models, such as rodents, but is not flexible enough for interrogating targets located beyond the mechanically fixed beam pattern. Perhaps, future research will focus on the continued development of confocal DF probes, such as that demonstrated by van Neer et al. [23], to further improve this imaging method. A fully confocal array design would significantly improve the limited depth of field of a cross-beam transducer (11 mm in this study), allowing for interrogation of larger targets. It is also possible that using DF transducers with transmit/receive frequencies lower than the 1.7/20 MHz used in this study will allow for deeper SHI. While lower frequencies will result in a larger diffraction limited resolution, we expect to recover resolution with ULM.

Another area that requires further exploration is the parameter space for motion correction based on sparsely interleaved b-mode acquisitions. FIGS. 12A and 12B show an example of the improvement in image quality provided by this algorithm, though we believe that most of the improvement in image quality is derived from simply discarding batches of frames associated with large physiological motions. It is possible that moving to a smaller ratio of SHI to b-mode frames will allow for higher fidelity speckle tracking based on the smaller decorrelation between b-mode frames of neighboring acquisitions. The in vivo images shown in this article were produced with a 100-to-1 ratio in which b-mode frames were separated temporally by 200 ms. This b-mode frame rate is sufficient for tracking respiratory motion but must be increased to fully sample the cardiac motion of the rodent model. It is difficult to quantify the performance of this motion correction approach in vivo because we lack ground truth information. Further studies may focus on characterizing this approach via simulations and in vitro.

This study also accomplished three-dimensional ULM in a similar fashion to the methods used by Lin et al. [9]. However, because of time constraints during imaging, a relatively large step size of 500 µm was used, which means the elevational resolution was orders of magnitude worse than the axial or lateral resolution. This sort of volume might be useful for evaluating metrics such as vascular density but will likely fall short for accurately assessing features such as tortuosity. However, this study highlights the potential of utilizing ULM for imaging whole organs in preclinical targets. Improvements in transducer technology might one day lead to fully sampled matrix arrays capable of ultrafast SHI for ULM.

V. CONCLUSION

SHI improves SNR by more than 10-dB in vitro compared with SVD filtering for average flow rates between 0.3 and 15.9 µm/frame. Since the method does not rely on motion to discriminate contrast from background signal, we expect SHI to work well even when MBs are stationary relative to tissue. Furthermore, SHI operates without the need to tune the singular vector threshold for each data set, which can be a cumbersome manual process. Baranger et al. [14] demonstrated that the most successful automatic threshold estimator for SVD filtering achieves optimal CTR for only roughly 60% of in vivo data sets. SHI, on the other hand, is a robust imaging scheme that requires a simple background noise threshold to produce images suitable for ULM processing. Furthermore, a relatively simple speckle-tracking scheme based on [29] applied over sparsely interleaved b-mode frames provides a framework for nonrigid displacement corrections without the need for optimizing a nonrigid transformation estimator such as [41]. SHI, therefore, offers a straightforward approach to bubble detection for ULM, even for challenging imaging scenarios, such as in the presence of slow flow or physiological motion.

The following section illustrates the use of superharmonic imaging to image a molecularly targeted contrast agent bound to a target molecule in vivo.

Super-Resolution Mapping of Molecularly Targeted Ultrasound Contrast Bound in vivo using Superharmonic Imaging In vivo biomarker expression can be measured with ultrasound molecular imaging and targeted microbubbles (MB). Conventional molecular imaging is constrained by diffraction-limited resolution. Our objective was to create super-resolution maps of targeted MB bound within blood vessels in vivo.

Statement of Contribution/Methods

Rodents were implanted with a subcutaneous fibrosarcoma tumor model. Images were acquired using a dual-frequency array transducer containing a 20 MHz high-frequency (HF) linear array outfitted with two 1.7 MHz elements that generated a low-frequency (LF) plane wave. Superharmonic (SH) imaging was accomplished by transmitting and receiving with the LF and HF elements, respectively. b-mode images were collected using the HF probe.

Animals received a bolus injection of 1E8 MB targeted to VEGFR2 by a heptapeptide. MB circulated for 5 minutes, then 1,000 SH frames were captured at 100 fps. Images were thresholded at 5 times the noise floor and convolved with a Laplacian of Gaussian kernel calibrated to the point spread function. The MB signal to noise floor ratio was 42 dB. MB were localized using a center of mass estimation and considered bound if they persisted for at least 30 consecutive frames without moving more than 2 microns. After the molecular imaging acquisition, conventional ultrasound localization microscopy (ULM) was performed via an infusion of non-targeted MB. 25,000 SH frames were captured at 500 fps. In both acquisitions, b-mode frames were interleaved for motion compensation. Rigid motion was estimated using the normalized correlation coefficient between each b-mode image and a reference frame; images with a correlation coefficient less than 0.9 were discarded. 3D scanning for data acquisition was achieved by translating the probe in elevation on a linear motion stage (4 mm scan, 1 mm step size).

Results/Discussion

Molecular targeting (FIG. 15B) was confined almost exclusively within the anatomical boundaries of the tumor (FIG. 15A). SH imaging was sensitive to bound MB because of its excellent CTR across all flow rates (42 dB in this experiment). This study provided proof-of-concept that targeted MB can be localized with superharmonic super-resolution imaging and was the first report of super-resolution ultrasound molecular imaging.

The disclosure of each of the following references is hereby incorporated herein by reference in its entirety

REFERENCES

[1] C. Errico et al., "Ultrafast ultrasound localization microscopy for deep super-resolution vascular imaging," *Nature*, vol. 527, no. 7579, pp. 499-502, November 2015.

[2] K. Christensen-Jeffries, R. J. Browning, M.-X. Tang, C. Dunsby, and R. J. Eckersley, "In Vivo acoustic super-resolution and super-resolved velocity mapping using microbubbles," *IEEE Trans. Med. Imag.*, vol. 34, no. 2, pp. 433-440, February 2015.

[3] Y. Desailly, J. Pierre, O. Couture, and M. Tanter, "Resolution limits of ultrafast ultrasound localization microscopy," *Phys. Med. Biol.*, vol. 60, no. 22, pp. 8723-8740, November 2015.

[4] P. Carmeliet and R. K. Jain, "Angiogenesis in cancer and other diseases," *Nature*, vol. 407, no. 6801, pp. 249-257, September 2000.

[5] D. Hanahan and R. Weinberg, "Hallmarks of cancer: The next generation," *Cell*, vol. 144, no. 5, pp. 646-674, March 2011.

[6] R. C. Gessner, S. R. Aylward, and P. A. Dayton, "Mapping microvasculature with acoustic angiography yields quantifiable differences between healthy and tumor-bearing tissue volumes in a rodent model," *Radiology*, vol. 264, no. 3, pp. 733-740, September 2012.

[7] S. E. Shelton et al., "Quantification of microvascular tortuosity during tumor evolution using acoustic angiography," *Ultrasound Med. Biol.*, vol. 41, no. 7, pp. 1896-1904, July 2015.

[8] S. R. Rao, S. E. Shelton, and P. A. Dayton, "The 'fingerprint' of cancer extends beyond solid tumor boundaries: Assessment with a novel ultrasound imaging approach," *IEEE Trans. Biomed. Eng.*, vol. 63, no. 5, pp. 1082-1086, May 2016.

[9] F. Lin, S. E. Shelton, D. Espindola, J. D. Rojas, G. Pinton, and P. A. Dayton, "3-D ultrasound localization microscopy for identifying microvascular morphology features of tumor angiogenesis at a resolution beyond the diffraction limit of conventional ultrasound," *Theranostics*, vol. 7, no. 1, pp. 196-204, 2017.

[10] T. Opacic et al., "Motion model ultrasound localization microscopy for preclinical and clinical multiparametric tumor characterization," *Nature Commun.*, vol. 9, no. 1, pp. 1-13, 2018.

[11] O. Couture, V. Hingot, B. Heiles, P. Muleki-Seya, and M. Tanter, "Ultrasound localization microscopy and super-resolution: A state of the art," *IEEE Trans. Ultrason., Ferroelectr., Freq. Control*, vol. 65, no. 8, pp. 1304-1320, August 2018.

[12] C. Demene et al., "Spatiotemporal clutter filtering of ultrafast ultrasound data highly increases Doppler and ultrasound sensitivity," *IEEE Trans. Med. Imag.*, vol. 34, no. 11, pp. 2271-2285, November 2015.

[13] Y. Desailly, A.-M. Tissier, J.-M. Correas, F. Wintzenrieth, M. Tanter, and O. Couture, "Contrast enhanced ultrasound by real-time spatiotemporal filtering of ultrafast images," *Phys. Med. Biol.*, vol. 62, no. 1, pp. 31-42, January 2017.

[14] J. Baranger, B. Arnal, F. Perren, O. Baud, M. Tanter, and C. Demene, "Adaptive spatiotemporal SVD clutter filtering for ultrafast Doppler imaging using similarity of spatial singular vectors," *IEEE Trans. Med. Imag.*, vol. 37, no. 7, pp. 1574-1586, July 2018.

[15] B. Fagrell, A. Fronek, and M. Intaglietta, "A microscope-television system for studying flow velocity in human skin capillaries," *Amer. J. Physiol.-Heart Circulatory Physiol.*, vol. 233, no. 2, pp. H318-H321, August 1977.

[16] C. G. Caro, T. J. Pedley, R. C. Schroter, and W. A. Seed, *The Mechanics of the Circulation*. Cambridge, U.K.: Cambridge Univ. Press, 2012.

[17] J. Foiret, H. Zhang, T. Ilovitsh, L. Mahakian, S. Tam, and K. W. Ferrara, "Ultrasound localization microscopy to image and assess microvasculature in a rat kidney," *Sci. Rep.*, vol. 7, no. 1, pp. 1-12, 2017.

[18] A. Bouakaz, S. Frigstad, F. J. Ten Cate, and N. De Jong, "Super harmonic imaging: A new imaging technique for improved contrast detection," *Ultrasound Med. Biol.*, vol. 28, no. 1, pp. 59-68, January 2002.

[19] J.-J. Hwang and D. H. Simpson, "Two pulse technique for ultrasonic harmonic imaging," U.S. Pat. No. 5,951, 478, Sep. 14, 1999.

[20] G. A. Brock-Fisher, M. D. Poland, and P. G. Rafter, "Means for increasing sensitivity in non-linear ultrasound imaging systems," U.S. Pat. No. 5,577,505, Nov. 26, 1996.

[21] C. Tremblay-Darveau, R. Williams, L. Milot, M. Bruce, and P. N. Burns, "Visualizing the tumor microvasculature with a nonlinear plane-wave Doppler imaging scheme based on amplitude modulation," *IEEE Trans. Med. Imag.*, vol. 35, no. 2, pp. 699-709, February 2016.

[22] P. J. Phillips, "Contrast pulse sequences (CPS): Imaging nonlinear microbubbles," in *Proc. IEEE Ultrason. Symp., Int. Symp.*, vol. 2, October 2001, pp. 1739-1745.

[23] P. Van Neer, G. Matte, M. Danilouchkine, C. Prins, F. Van Den Adel, and N. De Jong, "Super-harmonic imaging: Development of an interleaved phased-array transducer," *IEEE Trans. Ultrason., Ferroelectr., Freq. Control*, vol. 57, no. 2, pp. 455-468, February 2010.

[24] R. C. Gessner, C. B. Frederick, F. S. Foster, and P. A. Dayton, "Acoustic angiography: A new imaging modality for assessing microvasculature architecture," *Int. J. Biomed. Imag.*, vol. 2013, pp. 1-9, January 2013.

[25] S. E. Shelton, B. D. Lindsey, P. A. Dayton, and Y. Z. Lee, "First-in-human study of acoustic angiography in the breast and peripheral vasculature," *Ultrasound Med. Biol.*, vol. 43, no. 12, pp. 2939-2946, December 2017.

[26] E. Cherin et al., "In Vitro superharmonic contrast imaging using a hybrid dual-frequency probe," *Ultrasound Med. Biol.*, vol. 45, no. 9, pp. 2525-2539, September 2019.

[27] J. K. Tsuruta, N. P. Schaub, J. D. Rojas, J. Streeter, N. Klauber-DeMore, and P. Dayton, "Optimizing ultrasound molecular imaging of secreted frizzled related protein 2 expression in angiosarcoma," *PLoS ONE*, vol. 12, no. 3, March 2017, Art. no. e0174281.

[28] B. D. Lindsey, J. D. Rojas, K. H. Martin, S. E. Shelton, and P. A. Dayton, "Optimization of contrast-to-tissue ratio and role of bubble destruction in dual-frequency contrast-specific 'acoustic angiography' imaging," in *Proc. IEEE Int. Ultrason. Symp. (IUS)*, September 2014, vol. 61, no. 10, pp. 1774-1777.

[29] J. Luo and E. E. Konofagou, "A fast normalized cross-correlation calculation method for motion estimation," *IEEE Trans. Ultrason., Ferroelectr., Freq. Control*, vol. 57, no. 6, pp. 1347-1357, June 2010.

[30] W. Walker and G. Trahey, "A fundamental limit on delay estimation using partially correlated speckle signals," *IEEE Trans. Ultrason., Ferroelectr., Freq. Control*, vol. 42, no. 2, pp. 301-308, March 1995.

[31] D. Espindola, R. M. DeRuiter, F. Santibanez, P. A. Dayton, and G. Pinton, "Quantitative sub-resolution blood velocity estimation using ultrasound localization microscopy ex-vivo and in-vivo," 2020, arXiv: 2001.10787. [Online]. Available: https://arxiv.org/abs/2001.10787

[32] N. De Jong, M. Emmer, A. Van Wamel, and M. Versluis, "Ultrasonic characterization of ultrasound contrast agents," *Med. Biol. Eng. Comput.*, vol. 47, no. 8, pp. 861-873, August 2009. N. De Jong, R. Comet, and C. Lancée, "Higher harmonics of vibrating gas-filled microspheres. Part one: Simulations," *Ultrasonics*, vol. 32, no. 6, pp. 447-453, November 1994.

[34] B. D. Lindsey, J. Kim, P. A. Dayton, and X. Jiang, "Dual-frequency piezoelectric endoscopic transducer for imaging vascular invasion in pancreatic cancer," *IEEE Trans. Ultrason., Ferroelectr., Freq. Control*, vol. 64, no. 7, pp. 1078-1086, July 2017.

[35] *Definity Package Insert*, Lantheus Med. Imag., North Billerica, MA, USA, 2015.

[36] *LUMASON Package Insert*, Bracco Imag., Monroe Township, NJ, USA, 2016.

[37] *OPTISON Package Insert*, GE Healthcare, Oslo, Norway, 2016.

[38] V. Hingot, C. Errico, B. Heiles, L. Rahal, M. Tanter, and O. Couture, "Microvascular flow dictates the compromise between spatial resolution and acquisition time in ultrasound localization microscopy," *Sci. Rep.*, vol. 9, no. 1, p. 2456, 2019.

[39] K. Christensen-Jeffries et al., "Microbubble axial localization errors in ultrasound super-resolution imaging," *IEEE Trans. Ultrason., Ferroelectr., Freq. Control*, vol. 64, no. 11, pp. 1644-1654, November 2017.

[40] I. G. Newsome, T. M. Kierski, and P. A. Dayton, "Assessment of the superharmonic response of microbubble contrast agents for acoustic angiography as a function of microbubble parameters," *Ultrasound Med. Biol.*, vol. 45, no. 9, pp. 2515-2524, September 2019.

[41] S. Harput et al., "Two-stage motion correction for super-resolution ultrasound imaging in human lower limb," *IEEE Trans. Ultrason., Ferroelectr., Freq. Control*, vol. 65, no. 5, pp. 803-814, May 2018.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for producing an image of contrast agent particles, at least some of which are stationary with respect to surrounding tissue, the method comprising:
    administering a contrast agent particle into at least one vessel;
    delivering, utilizing at least one ultrasound transducer having non-overlapping −6 dB first and second bandwidths for transmit and receive, a single ultrasound pulse having a first frequency range from the first bandwidth to the at least one vessel;
    detecting, utilizing the at least one ultrasound transducer and at a second frequency range from the second bandwidth ultrasound energy scattered from the contrast agent particle as a result of the single ultrasound pulse having the first frequency range being scattered by the contrast agent particle;
    converting the scattered ultrasound energy into an electronic radio frequency signal;
    using an algorithm to determine a spatial location of the contrast agent particle based on extraction of a specific feature of the radio frequency signal;
    generating an image by displaying a marker of the spatial location of the contrast agent particle, wherein the marker comprises at least one pixel; and
    repeating the detecting, converting, using, and generating for a plurality of contrast agent particles, at least some of which are stationary or moving at the same velocity with respect to surrounding tissue, until sufficient markers have been accumulated to reconstruct a pattern, which is an image of the contrast agent particles, including the particles that are stationary or moving at the same velocity with respect to the surrounding tissue and located within at least one vessel, and the image of the contrast agent particles forms an image of the at least one vessel and has a resolution that is finer than a pulse length of the ultrasound pulse.

2. The method of claim 1 wherein a resolution of the image is at least twice as fine as the pulse length of the ultrasound pulse.

3. The method of claim 1 wherein the at least one vessel comprises a blood vessel, a lymphatic vessel, or part of a venous or capillary network in a human body.

4. The method of claim 1 wherein endothelial cells within the at least one vessel express a biomarker which causes the contrast agent particles to adhere to a wall of the at least one vessel.

5. The method of claim 1 wherein the pattern is an image of contrast agent particle distribution within vessels of tissue, an organ, or a tumor.

6. The method of claim 1 wherein the mean or the median of the second frequency range detected is at least double or at least triple the mean or the median of the first frequency range.

7. The method of claim 1 wherein the at least one ultrasound transducer has non-overlapping −12 dB bandwidths for transmit and receive.

8. The method of claim 1 wherein the contrast agent particles include at least one of microbubbles and nanobubbles.

9. The method of claim 1 wherein at least some of the contrast agent particles comprise a liquid perfluorocarbon core prior to ultrasound exposure.

10. The method of claim 1 wherein the algorithm applies high pass filtering, and after the high pass filtering, applies a thresholding operation.

11. The method of claim 1 wherein the algorithm includes detecting a centroid of the radio frequency signal, wherein the centroid of the radio frequency signal is defined a center of mass or a peak of the radio frequency signal.

12. The method of claim 1 wherein the algorithm includes detecting an onset of the radio frequency signal, wherein the onset of the radio frequency signal is defined as a beginning of the radio frequency signal.

13. The method of claim 1 wherein the algorithm allows calculation of a velocity and a direction of the contrast agent particle.

14. The method of claim 1 wherein the algorithm determines the spatial location of the contrast agent particle without using a singular value decomposition filter.

15. The method of claim 1 wherein the contrast agent particles include at least some particles targeted to and bound with a molecule in vivo and wherein generating the image includes generating an image of the contrast agent targeted to and bound with the molecule in vivo.

16. The method of claim 1 wherein the ultrasound pulse having a first frequency range is transmitted with zero phase delay across a plurality of elements of a transmitting transducer to emit a plane wave into the at least one vessel.

17. The method of claim 1, wherein the first frequency range is between 0.5 and 5 MHz, and the second frequency range is between 5 and 50 MHz.

18. A system for producing an image of contrast agent particles, at least some of which are stationary with respect to surrounding tissue, the system comprising:
    at least one ultrasound transducer having non-overlapping −6 dB first and second bandwidths for transmit and receive, the at least one ultrasound transducer for delivering single ultrasound pulse having a first frequency range from the first bandwidth to at least one vessel infused with a contrast agent particle, for detecting, at a second frequency range from the second bandwidth, ultrasound energy scattered from the contrast agent particle as a result of the single ultrasound pulse having the first frequency range being scattered by the contrast agent particle, and for converting the scattered ultrasound energy into an electronic radio frequency signal; and
    a super-resolution processor for: using an algorithm to determine a spatial location of the contrast agent particle based on extraction of a specific feature of the radio frequency signal; generating an image by displaying a marker of the spatial location of the contrast agent particle, wherein the marker comprises at least one pixel; and repeating the detecting, converting, using, and generating for a plurality of contrast agent particles, at least some of which are stationary or moving at the same velocity with respect to the surrounding tissue, until sufficient markers have been accumulated to reconstruct a pattern, which is an image of the contrast agent particles, including the particles that are stationary or moving at the same velocity with respect to the surrounding tissue and located within the at least one vessel, and the image of the contrast agent particles forms an image of the at least one vessel that has a resolution that is finer than a pulse length of the ultrasound pulse.

19. The system of claim 18 wherein a resolution of the image is at least twice as fine as the pulse length of the ultrasound pulse.

20. The system of claim 18 wherein the at least one vessel comprises a blood vessel, a lymphatic vessel, or part of a venous or capillary network in a human body.

21. The system of claim 18 wherein endothelial cells within the at least one vessel express a biomarker which causes the contrast agent particles to adhere to a wall of the at least one vessel.

22. The system of claim 18 wherein the pattern is an image of contrast agent particle distribution within vessels of tissue, an organ, or a tumor.

23. The system of claim 18 wherein the mean or the median of the second frequency range detected is at least double or at least triple the mean or the median of the first frequency range.

24. The system of claim 18 wherein the at least one ultrasound transducer has non-overlapping −12 dB bandwidths for transmit and receive.

25. The system of claim 18 wherein the contrast agent particles include at least one of microbubbles and nanobubbles.

26. The system of claim 18 wherein the at least some of the contrast agent particles comprise a liquid perfluorocarbon core prior to ultrasound exposure.

27. The system of claim 18 wherein the algorithm applies high pass filtering, and, after the high-pass filtering, applies a thresholding operation.

28. The system of claim 18 wherein the algorithm includes detecting a centroid of the radio frequency signal, wherein the centroid of the radio frequency signal is defined as a center of mass or a peak of the radio frequency signal.

29. The system of claim 18 wherein the algorithm includes detecting an onset of the radio frequency signal, wherein the onset of the radio frequency signal is defined as a beginning of the radio frequency signal.

30. The system of claim 18 wherein the algorithm allows calculation of a velocity and a direction of the contrast agent particle.

31. The system of claim 18 wherein the algorithm determines the spatial location of the contrast agent particle without using a singular value decomposition filter.

32. The system of claim 18 wherein the contrast agent particles include at least some particles targeted to and bound with a molecule in vivo and wherein generating the image includes generating an image of the contrast agent targeted to and bound with the molecule in vivo.

33. The system of claim 18 wherein the ultrasound pulse having a first frequency range is transmitted with zero phase delay across a plurality of elements of the ultrasound transducer to emit a plane wave into the at least one vessel.

34. The system of claim 18 wherein the first frequency range is between 0.5 and 5 MHz, and the second frequency range is between 5 and 50 MHz.

35. A non-transitory computer readable medium having stored thereon executable instructions that when executed by a processor of a computer control the computer to perform steps comprising:
controlling at least one ultrasound transducer having non-overlapping −6 dB first and second bandwidths for transmit and receive for delivering a single ultrasound pulse having a first frequency range from the first bandwidth to at least one vessel infused with a contrast agent,
detecting, utilizing the at least one ultrasound transducer and at a second frequency range from the second bandwidth, ultrasound energy scattered from the contrast agent particle as a result of the single ultrasound pulse having the first frequency range being scattered by the contrast agent particle;
converting the scattered ultrasound energy into an electronic radio frequency signal;
using an algorithm to determine a spatial location of the contrast agent particle based on extraction of a specific feature of the radio frequency signal;
generating an image by displaying a marker of the spatial location of the contrast agent particle, wherein the marker comprises at least one pixel; and
repeating the detecting, converting, using, and generating for a plurality of contrast agent particles, at least some of which are stationary or moving at the same velocity with respect to surrounding tissue, until sufficient markers have been accumulated to reconstruct a pattern, which is an Image of the contrast agent particles, including the particles that are stationary or moving at the same velocity with respect to the surrounding tissue and located within the at least one vessel, and the image of the contrast agent particles forms an image of the at least one vessel that has a resolution that is finer than a pulse length of the ultrasound pulse.

36. The method of claim 1 wherein the at least one vessel is in an anatomical region in which the at least one vessel moves because of cardiac motion or respiration, and generating the image includes removing artifacts caused by the cardiac motion or respiration.

37. The system of claim 18 wherein the at least one vessel is in an anatomical region in which the at least one vessel moves because of cardiac motion or respiration, and generating the image includes removing artifacts caused by the cardiac motion or respiration.

38. The non-transitory computer readable medium of claim 35 wherein the at least one vessel is in an anatomical region in which the at least one vessel moves because of cardiac motion or respiration, and generating the image includes removing artifacts caused by the cardiac motion or respiration.

* * * * *